United States Patent [19]

Bird

[11] 4,020,834
[45] May 3, 1977

[54] RESPIRATOR AND METHOD

[76] Inventor: Forrest M. Bird, 212 NW. Cerritos, Palm Springs, Calif. 92262

[22] Filed: May 16, 1975

[21] Appl. No.: 578,170

[52] U.S. Cl. .......................................... 128/145.6
[51] Int. Cl.² ...................................... A61M 16/00
[58] Field of Search ......... 128/145.8, 145.6, 145.5, 128/146.5, 188

[56] References Cited

UNITED STATES PATENTS

| 2,121,311 | 6/1938 | Anderson et al. | 128/145.8 |
| 3,072,327 | 1/1963 | Perry | 128/145.8 |
| 3,156,238 | 11/1964 | Bird et al. | 128/188 |
| 3,537,450 | 11/1970 | Fox | 128/145.6 |
| 3,669,108 | 6/1972 | Sunblom et al. | 128/145.8 |
| 3,730,180 | 5/1973 | Davison | 128/145.6 |
| 3,768,469 | 10/1973 | Myers | 128/145.8 |
| 3,831,595 | 8/1974 | Valenta et al. | 128/145.8 |
| 3,840,006 | 10/1974 | Buck et al. | 128/145.8 |
| 3,903,881 | 9/1975 | Weigl | 128/145.8 |
| 3,905,362 | 9/1975 | Eyrick et al. | 128/145.8 |

OTHER PUBLICATIONS

Downs et al., Intermittent Mandatory Ventilation: A New Approach to Weaning Patients from Mechanical Ventilators, 3/26/72.

Primary Examiner—Robert W. Michell
Assistant Examiner—Henry J. Recla
Attorney, Agent, or Firm—Flehr, Hohbach, Test, Albritton & Herbert

[57] ABSTRACT

A respirator with an inhalation phase and an exhalation phase in its operative cycle having an inlet adapted to be connected to a supply of gas under pressure and first and second outlets.

A device is provided for establishing a positive pressure above atmospheric against which the patient must exhale during the exhalation phase for a predetermined period near the end of the exhalation phase. A device is provided for terminating the application of positive pressure so that the patient is exposed to ambient atmospheric pressure prior to initiation of the inhalation phase. Inspiratory flow acceleration means is provided for supplying additional gases to the first outlet during the inhalation phase. A control device is provided for establishing the length of the inhalation phase and includes an auxiliary reservoir for collecting gas and means for bleeding off the gas from the auxiliary reservoir whereby the exhalation time can be adjusted without being adversely affected by the pressure of the inlet gas. A volume limiting device is provided so that when desired a precise volume of gas can be delivered to the patient. A device is provided for supplying an anesthesia gas in the gases supplied to the inlet so that the respirator can be utilized as an anesthesia unit.

32 Claims, 16 Drawing Figures

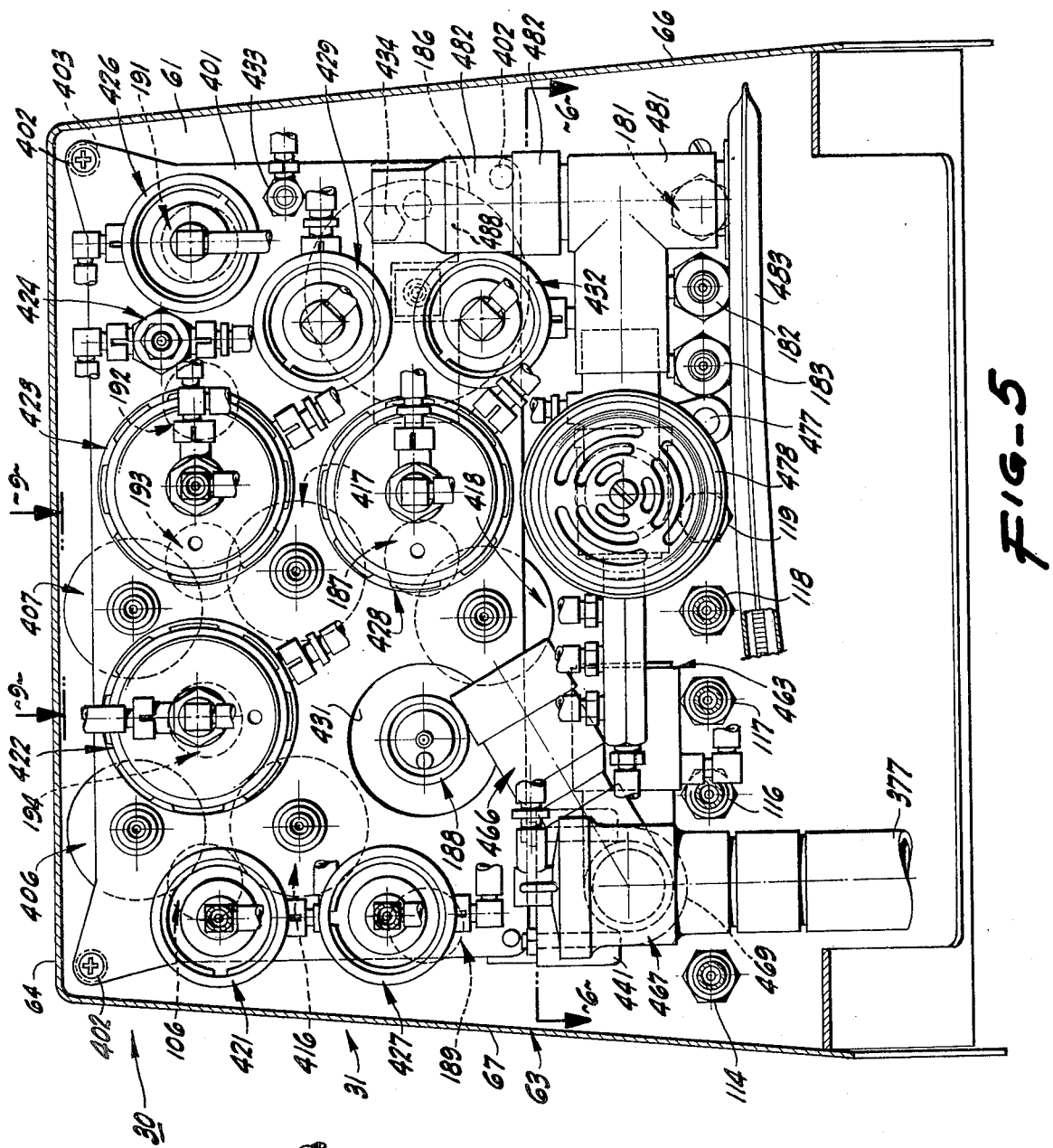
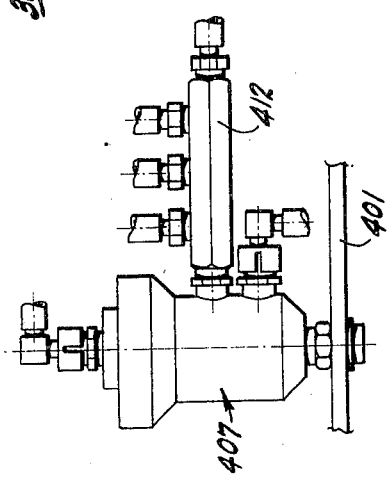
FIG-5
FIG-9

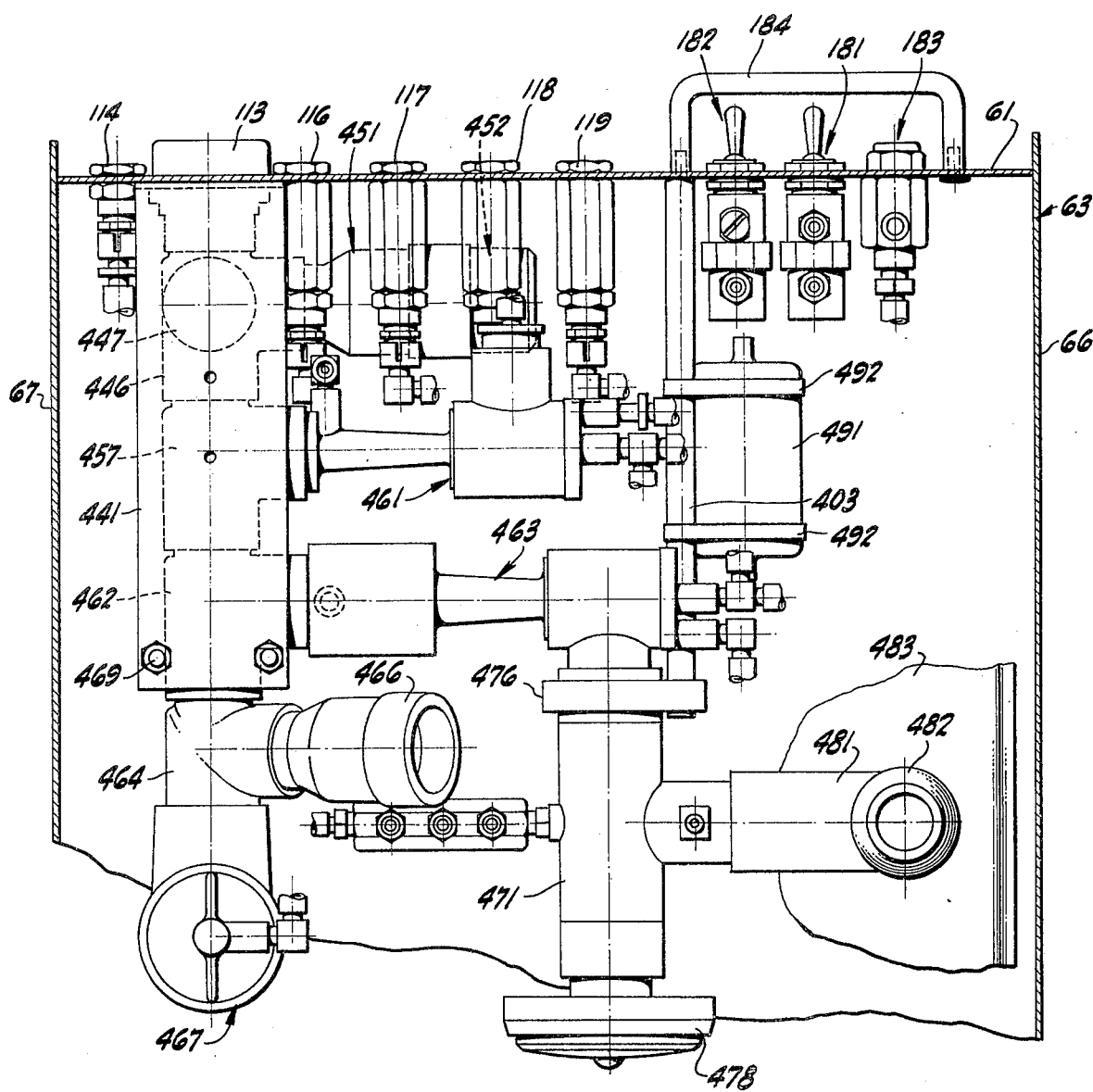

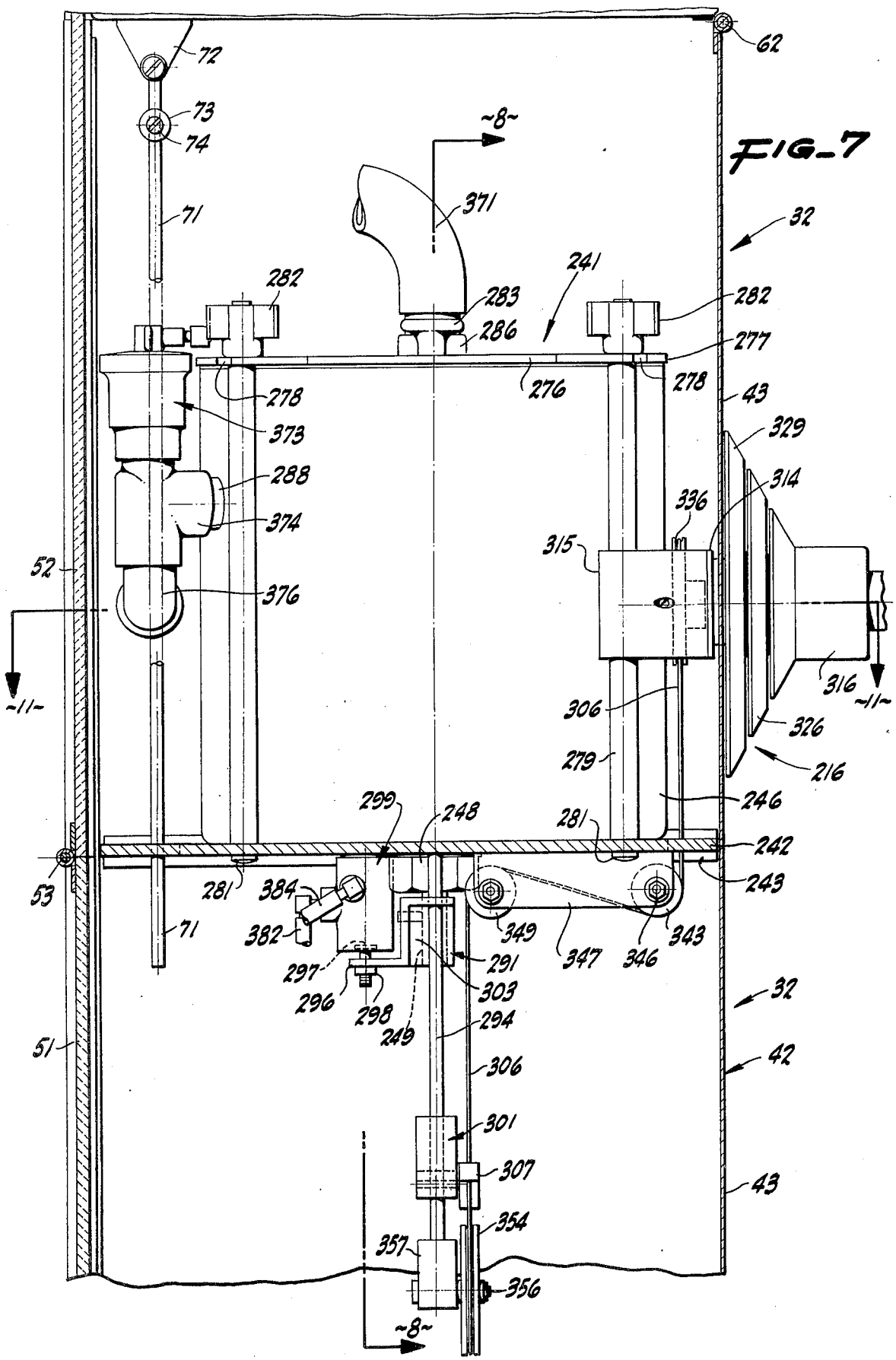

FIG_14

19,834

RESPIRATOR AND METHOD

BACKGROUND OF THE INVENTION

Various types of ventilators and respirators have heretofore been provided. Many of such ventilators and respirators have been unduly complicated and expensive, and in addition have lacked the desired versatility. For example, they have lacked means for applying a positive pressure above atmospheric against which a patient must exhale near the end of the exhalation phase and means for terminating the positive pressure against which the patient must exhale so that the patient is exposed to ambient pressure prior to initiation of the inhalation phase. They have also lacked other adjustments. In addition, it has in the past been unduly expensive to provide volume limiting capabilities which can be used in conjunction with the respirator to provide an anesthesia unit. There is therefore a need for a new and improved respirator and method which overcomes the above disadvantages.

SUMMARY OF THE INVENTION AND OBJECTS

The respirator has an inhalation phase and an exhalation phase in its operative cycle and consists of an inlet adapted to be connected to a supply of gas under pressure and first and second outlets. A sequencing servo is provided which has an inlet and an outlet and control valve means disposed therein movable between open and closed positions to control the flow of gas from the inlet to the outlet of the sequencing servo. The control valve means is in an open or one position during the inhalation phase of the respirator and in a closed or off position during the exhalation phase of the ventilator. Means is provided for connecting the inlet of the respirator to the inlet of the sequencing servo and for connecting the outlet of the sequencing servo to the first outlet of the respirator. A patient adapter is provided and means is also provided for supplying gas from the first outlet of the respirator to the patient adapter. An exhalation valve assembly is coupled to the patient adapter and is movable between open and closed positions. Means is provided for supplying gas from the inlet of the respirator to the second outlet of the respirator and means is provided for connecting the second outlet of the respirator to the exhalation valve assembly to maintain the exhalation valve assembly in a closed position during the inhalation phase. Means is provided for sensing the pressure of the gas in the first outlet and for switching the sequencing servo from an open position to a closed position when a predetermined pressure is reached in the first outlet. Means is provided for establishing a positive pressure above atmospheric against which the patient must exhale during the exhalation phase and which may be applied only during a predetermined portion of the exhalation phase. Means is also provided for terminating the application of the positive pressure so that the patient is exposed to ambient atmospheric pressure prior to the initiation of the inhalation phase. Control means is provided for establishing the length of the inhalation phase and includes an auxiliary reservoir and orifice means for supplying gas from an auxiliary reservoir. Volume limiting means is provided whereby a precise volume can be delivered to the lungs of the patient.

In general, it is an object of the present invention to provide a respirator and method which is of the modular type and which has incorporated therein many features which makes it useful as an anesthesia unit as well as a respirator.

Another object of the present invention is to provide a respirator and method of the above character which is relatively inexpensive to manufacture and can be readily repaired.

Another object of the invention is to provide a respirator of the above character in which a control is provided which requires the patient to exhale against a positive pressure above atmospheric during a predetermined portion of the exhalation phase.

Another object of the invention is to provide a respirator and method of the above character in which control is provided for terminating the application of the positive pressure against which the patient must exhale so that the patient is exposed to ambient atmospheric pressure prior to the initiation of an inhalation phase.

Another object of the invention is to provide a respirator and method of the above character in which a precise volume of gas can be delivered to the patient when desired.

Another object of the invention is to provide a respirator and method of the above character in which a bellows assembly is utilized and when in inhalation phase, the inspiratory gases are utilized to raise the bellows to deliver gases in the bellows to the patient and thereafter these same inspiratory gases are transferred into the bellows during the exhalation phase for delivery to the patient during the next inspiratory phase.

Another object of the invention is to provide a respirator and method of the above character in which there is no significant surge in inspiratory pressure at the end of the inhalation phase as gases are released from outside of the bellows to flow into the inside of the bellows.

Another object of the invention is to provide a respirator and method of the above character in which a relatively simple compound dial assembly is utilized for computing the proper volume to be delivered to the patient.

Another object of the invention is to provide a respirator and method of the above character in which such factors as compliance, air density and the like are removed as significant factors by use of the compound dial assembly in delivering the desired volume of gas to the patient.

Another object of the invention is to provide a respirator of the above character in which the bellows assembly can be readily removed for aseptic purposes.

Another object of the invention is to provide a respirator and method of the above character in which the length of the exhalation phase can be readily adjusted to extend over relatively long periods of time.

Another object of the invention is to provide a respirator and method of the above character in which the exhalation time can be adjusted over relatively long periods of time with relatively simple controls.

Another object of the invention is to provide a respirator and method of the above character in which an automatic back-up is provided to supply a mandated volume should the patient fail to take a spontaneous breath.

Another object of the invention is to provide a respirator and method which has an automatic sensitivity circuit which will institute an inspiratory phase if the pressure in the breathing circuit should drop to below a predetermined value.

Another object of the invention is to provide a respirator and method of the above character in which an intermittent mandatory volume control is utilized on conjunction with an intermittent mandatory volume assist.

Another object of the invention is to provide a respirator and method of the above character in which intermittent mandatory ventilation can be provided.

Another object of the invention is to provide a respirator and method of the above character which makes it possible for a patient to take spontaneous breaths before a mandated volume is delivered to the patient.

Another object of the invention is to provide a respirator and method of the above character which makes it possible for the patient to obtain gases on demand even though the pressure does not drop to ambient.

Another object of the invention is to provide a respirator and method of the above character which makes it possible to obtain gases on demand with relatively little effort.

Another object of the invention is to provide a respirator and method of the above character in which an automatic reset is provided for termination of inspiration.

Another object of the invention is to provide a respirator and method of the above character in which automatic gas balancing is provided when the respirator is utilized as an anesthesia unit.

Another object of the invention is to provide a respirator and method of the above character which has automatic refill means when the respirator is utilized as an anesthesia unit.

Another object of the invention is to provide a respirator and method of the above character in which means has been provided for accumulating supplemental gas during the exhalation phase so that it is available during the inhalation phase to supplement the normal inspiratory flow of gases.

Additional objects and features of the invention will appear from the following description in which the preferred embodiments are set forth in detail in conjunction with the accompanying drawings.

BRIEF DESCRIPTION OF THE DRAWINGS

FIG. 5 is a cross-sectional view taken along the line 5—5 of FIG. 4.

FIG. 6 is a cross-sectional view taken along the line 6—6 of FIG. 5.

FIG. 7 is an enlarged cross-sectional view of a portion of the lower cabinet or module and the parts provided therein.

FIG. 9 is a view looking along the line 9—9 of FIG. 5.

DESCRIPTION OF THE PREFERRED EMBODIMENTS

Figure 1:
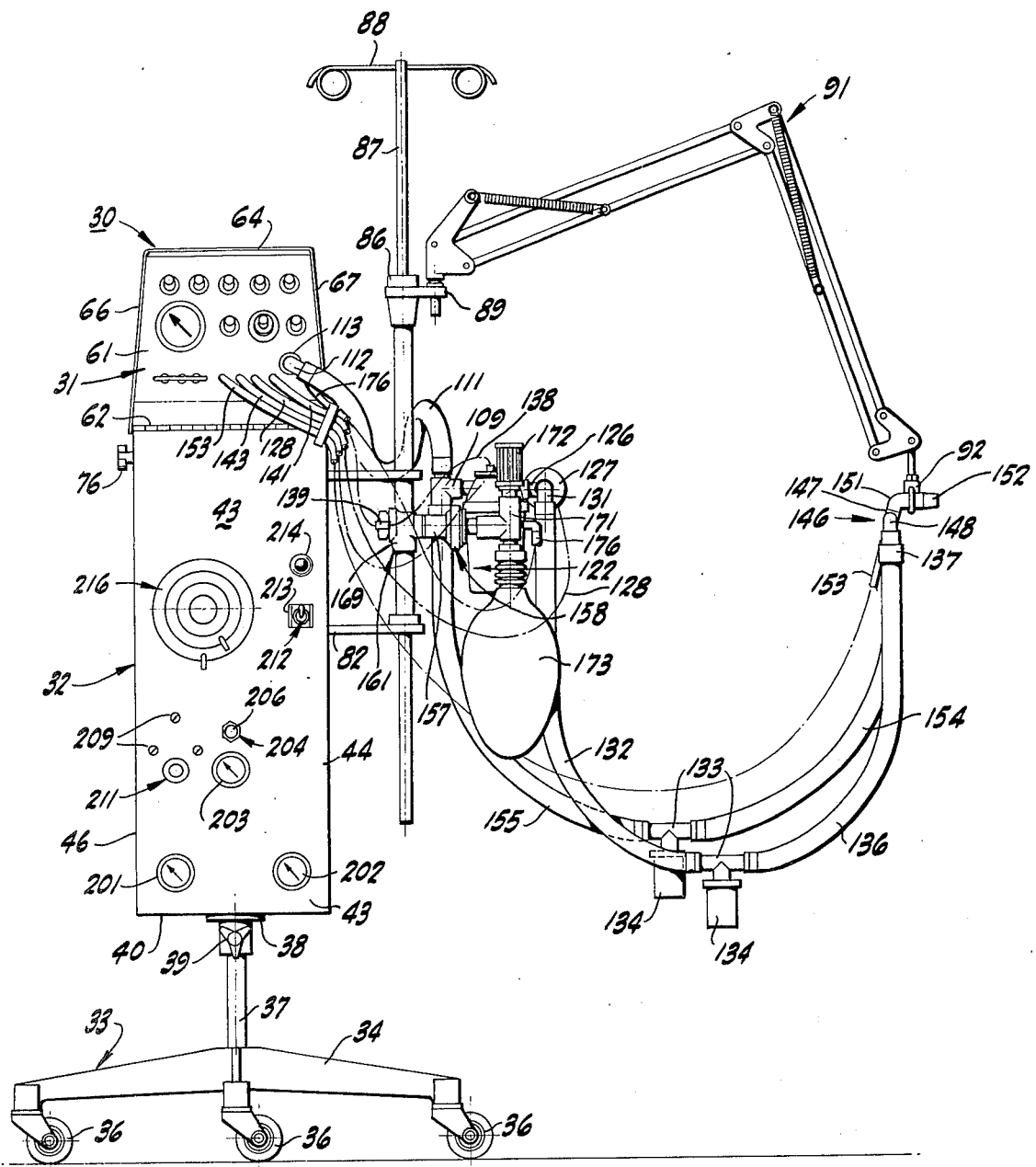
FIG. 1 is a front elevational view of a respirator incorporating the present invention.

The respirator 30 incorporating the invention and used in conjunction with the present method consists of an upper cabinet 31 mounted upon a lower cabinet 32. The lower cabinet 32 is supported in a suitable manner such as by a castered stand 33. The stand 33 consists of a fourlegged base 34 which is provided with four castered wheels 36 on the outer extremities of the same. The base 34 is provided with an upstanding post 37 which is mounted in a fitting 38 secured to the bottom of the lower cabinet 32. An adjustable screw 39 is provided for securing the upper end of the post within the fitting 38.

The lower cabinet 32 consists of a bottom wall 41 upon which there is mounted a U-shaped sheet metal member 41 that forms a front wall 43 and side walls 44 and 46. It is also provided with a rear wall 47. Bottom and side channels 48 and 49 are carried by the rear wall 47 and slidably receive a transparent panel 51 formed of a suitable material such as plastic. Another similar panel 52 is provided for the upper part of the rear side of the lower cabinet 32 and is hinged to the lower panel 51 by piano-type hinge 53. The panel 52 is provided with a metal trim 54 surrounding the sides and the upper edges of the same. The upper end of the panel 52 is adapted to be engaged by a U-shaped chanel 56 carried by the upper cabinet 31 to retain it in place. The upper panel 52 is provided with a handle 57 which is adapted to be engaged by the hand when it is desired to swing the same to an open position about the hinge 53.

The upper cabinet 31 consists of a front panel 61 which is secured by a piano-type hinge 62 to the upper portion of the front wall of the lower cabinet 32. The front panel 61 is secured to a U-shaped sheet metal member 63 which forms a top wall 64 and side walls 66 and 67. A rear wall 68 is carried by the U-shaped member 63 and is provided with a handle 69 to permit the upper cabinet 31 to be lifted about the pivot point formed by the hinge 62 to permit the panel 53 to be swung outwardly and downwardly to obtain access to the interior of the lower cabinet.

Means is provided for supporting the upper cabinet 31 in a tilted position with respect to the lower cabinet 32 and consists of a rod 71 (see FIG. 7) which is pivotally connected to a bracket 72 secured to the side wall 66 of the upper cabinet 31. The rod 71 extends through a collar 73 through which there extends a screw 74 mounted upon the side wall 44 and which is provided with a knob 76 accessible from the exterior (see FIG. 1) so that it can be tightened to engage the rod 71 to hold it in a desired position.

The respirator 30 includes additional apparatus which is mounted outside of the upper and lower cabinets 31 and 32. Thus as shown in the drawing, there is provided two support arms 81 and 82 which are mounted on the side wall 46 of the lower cabinet or case 32 and extend outwardly at right angles thereto. A large support tube 83 is mounted in the outer ends of the support arms 81 and 82 and is secured therein by a suitable means such as set screws (not shown). A fitting 86 is mounted on the upper end of the support tube 83. A support rod 87 extends through the fitting 86 and through the support tube 83 and is held in a desired elevated position by a set screw (not shown) provided by the fitting 86. A wire-like support member 88 is carried by the upper end of the support rod 87 and can be utilized for supporting various types of equipment such as I.V. bottles and the like. The fitting 86 is provided with an ear 89 in which there is mounted on adjustable support arm assembly 91. The support arm assembly 91 carries a clamp 92 which is utilized for a purpose hereinafter described. A collar 93 is mounted on the support tube 83 and carries a pair of depending hooks 94 which can be utilized for supporting various types of equipment utilized in conjunction with the respirator.

A quick disconnect fitting 101 (see FIG. 3) is secured to the support tube 83 by a screw 102 carrying a knob 103. A spring operated plunger 104 carried by the fitting 101 is adapted to engage a part 106 which is slidably received within the fitting 101 and retained therein by the plunger 104 engaging a hole (not shown) in the part 106. When it is desired to remove the part 106, it is merely necessary to lift the plunger 104 to release the part. The part 106 carries a tee 107. Another tee 108 is mounted in one leg of the tee 107 and has connected thereto a large flexible breathing tube 111. The breathing tube 111 is provided with a fitting 112 which is mounted by a slip fit in a breathing tube receptacle 113 provided on the front panel 61 of the upper cabinet 31 (see FIG. 2). The front panel 61 is provided with five additional fittings or receptacles 114, 116, 117, 118 and 119 in which the 114 can be identified as the expiratory gradient fitting, 116 as the inspiratory power fitting, 117 as the inspiratory nebulization fitting, 118 as the I.M.V. nebulization fitting and 119 as the airway pressure fitting.

Air supplied through the breathing tube 111 flows through the tee 108. One leg of the tee 108 is connected into a cap 212 of a 500 c.c. nebulizer of the type described in U.S. Pat. No. 3,172,406. The nebulizer herein utilized is like the one described in that patent with the exception that two nebulizer jets are provided in the cap 121 rather than just the single nebulizer jet disclosed in the patent. A tee 126 is carried by the cap 121 and is disposed directly opposite the tee 108. A nebulizer 127 of the type described in U.S. Pat. No. 3,172,406 is mounted in one leg of the tee 126. As described in that patent, the nebulizer 127 is provided with a nozzle which is connected to a flexible tube 128 (see FIG. 3) that is connected to a fitting 129 mounted in the inspiratory nebulization socket 117. A fitting 131 is mounted in the remaining leg of the tee 126 and is connected to a large flexible breathing tube 132. The breathing tube 132 is connected to one leg of the tee 133. A water trap assembly 134 of the type described in copending application Ser. No. 534,852 filed Dec. 20, 1974, now abandoned, is mounted on one leg of the tee 133 and is utilized for collecting vapors which have condensed within the breathing tube 132. A large breathing tube 136 is connected to the other leg of the tee 133 and is connected to a fitting 137.

One of the nebulizer jets of the 500 c.c. nebulizer 122 is connected by a tube 138 to a tee 139 (see FIG. 1). The tee 139 is connected by a tube 141 to a fitting 142 which is mounted in the socket 116 identified as inspiratory power on the front panel 61. The other of the nebulizer jets in the 500 c.c. nebulizer 122 is connected by a tube 143 to a fitting 144 mounted in the I.M.V. nebulization service socket 118.

A swivel unit 146 is mounted on the fitting 137. The swivel unit 146 is provided with a central body 147 on which there is mounted a swivel 148 which can rotate on the body and which is mounted in the fitting 137. Another swivel (not shown) is mounted on the other end of the body for swiveling motion thereon. A fitting 151 is swivel mounted on the center of the body 147. A patient adapter or mouthpiece 152 is secured to the fitting 151. A small tube 153 is also connected to the body 147 and is in communication with the interior of the body 147. The tube 153 is connected to a fitting 154 mounted in the receptacle 119 identified by "airway pressure" on the front panel 61. The swivel 149 is connected to a large tube 154. The swivel unit 146 makes it possible for the patient to move about with relative ease because of the swivel mounted provided for the patient adapter 152 and also the swivels 148 and 149 provided for the large tubes 136 and 154. The large tube 154 is connected by a fitting 156 to one leg of the tee 107 (see FIG. 3). The tee 107 is provided with a pair of shuttle valves of the type identified as shuttle valves 513 and 514 in U.S. Pat. No. 3,842,828.

Exhalation gases passing through the large tube 154 pass through the lower shuttle valve and into the tee 107 and then out one of the legs of the tee 107 to a fitting 157 provided as a part of a valve assembly 158 of the type described in U.S. Pat. No. 3,842,828. An exhalation valve assembly 161 is mounted on the valve assembly 158. The exhalation valve assembly 161 is of the type described in U.S. Pat. No. 3,688,794. As described therein, it includes a spring urged valve normally closed member (not shown) which is adapted to be moved into and out of engagement with a valve seat. A diaphragm (not shown) is provided which when pressure is applied thereto retains the valve member in a closed position. The tee 139 (see FIG. 1) is mounted on the exhalation valve assembly 161 and is connected to a fitting 142 which is mounted in the inspiratory power socket or fitting 116 provided in the front panel 61 as hereinbefore described.

The tube 154 is connected to a tee 133 which has a water trap 134 mounted thereon. The tee 133 is connected to another large tube 155 which is connected to the fitting 156 which is connected to the tee 107. The exhalation valve assembly 161 is provided with a downwardly depending extension 169 which is open to the atmosphere.

A tee 171 is mounted on the valve assembly 158. A muffler 172 is mounted in one leg of the tee 171. A compression bulb 173 is connected to the remaining leg of the tee 171. The compression bulb 173 is of a conventional type and is formed of a suitable material such as rubber and is adapted to be compressed by hand as hereinafter described. A small nozzle (not shown) is provided in the tee 171 and is in alignment with the leg of the tee connected to the valve assembly 158. A tube 176 is connected to the nozzle in the tee 171 and to a fitting 177 which is mounted in the expiratory gradient socket 114 on the front panel 61.

A plurality of additional controls and the like are provided on the front panel 61 of the respirator 30 and include two toggle switches 181 and 182 and a metering valve 183. The toggle switch 181 can be identified as an I.M.V. assist toggle switch and toggle switch 182 can be identified as an I.M.V. switch in which I.M.V. stands for intermittent mandatory ventilation. The metering valve 183 can be adjusted by an Allen head wrench. A U-shaped rod 184 is mounted on the front panel and overlies the toggle switches 181 and 182 and fitting 183 and serves to prevent a person from accidentally hitting the toggle switches and moving them to different positions.

A manometer 186 is mounted on the front panel and is provided for monitoring the pressure in the airway supplied through the breathing tube receptacle 113. An expiratory time control valve assembly 187 is mounted on the front panel 61. A sequencing servo cartridge 188 is mounted on the front panel as is an inspiratory time control valve assembly 189. Near the top of the front panel 61 from left to right there is provided an expiratory flow gradient control valve assembly 191, an expiratory flow gradient delay control valve assembly 192, an apneustic control valve assembly 193, an inspiratory flow acceleration control valve assembly 194 and an inspiratory flow rate control valve assembly 196.

A collar 178 is fitted over the small five tubes which are connected to the receptacles 114, 116, 117, 118 and 119 and serves to maintain the arrangement of the tubes when the tubes are disconnected from the front panel 61. A pair of gauges 201 and 202 which are mounted on the lower extremity of the front panel 43. Gauge 201 is an oxygen gauge and gauge 202 is an air gauge. An operating pressure gauge 203 is also provided on the front panel 43. Immediately above the operating pressure 203 there is provided a master on-off switch assembly 204 which is provided with a control knob 206 that is accessible on the front panel 43. A gas blender 208 of the type described in U.S. Pat. No. 3,737,627 is mounted within the lower cabinet 32 by suitable means such as screws 209 which secure it to the front panel 43. The gas blender 208 is provided with a control knob 211 which is accessible from the front side of the front panel 43.

A toggle switch assembly 212 is provided on the front panel for selecting either a volume limited delivery or pressure or time limited delivery as hereinafter described. A U-shaped guard 213 is mounted on the front panel to prevent someone from accidently knocking the toggle switch 212 from one position to another. A wink light 214 is also mounted on the front panel 43 immediately above the toggle switch assembly 212. The wink light is of a suitable type such as one manufactured by Norgren Fluidics of Littleton, Colorado. For example, it can be one which is normally black and which turns to green when a pressure is applied to the same. A compound knob assembly 216 is also mounted on the front panel 43.

The respirator 30 is connected to suitable gas supplies. For example, a line 221 is provided which is connected to a supply of oxygen under suitable pressure as, for example, 50 to 70 psi. The lines 221 and 222 are connected to filters 223 and 224 of a conventional type which are mounted in the rear wall 47 of the lower cabinet 42. The filter 223 is connected by a tube 226 to the gauge 201. It is also connected to a tube 227 to the blender 208. The filter 224 is connected by a tube 228 to the gauge 202 so that the gauge 202 measures the pressure of the incoming air. The output of the filter is also connected by a tube 229 to the blender 208. The output of the blender 208 is connected by a tube 231 to a pressure regulator 232 of a conventional type which is utilized for reducing the pressure to approximately 50 psi which is a desired operating pressure for the gases to be supplied to the apparatus. The output of the regulator 232 is connected by a tube 233 to the inlet of the master on-off switch 204. The output of the master on-off switch 204 is connected by a tube 234 to the gauge 203 which gives a reading on the operating of the pressure of the mixed gases being supplied to the respirator. The master on-off switch 204 is also connected by a tube 236 to the upper cabinet 31 for a purpose hereinafter described.

A bellows assembly 241 is mounted in the upper portion of the lower cabinet 32. The bellows assembly consists of a flat deck plate 242 which is mounted in a pair of U-shaped guides 243 mounted on the side walls 44 and 46 by screws (not shown). As can be seen, the deck plate 242 is mounted in such a manner as it can be removed from the rear after the panels 51 and 52 have been removed. Normally, the deck plate 242 is retained within the bottom cabinet by screws (not shown) extending through the front wall 43.

A cylindrical canister 246 which is open at the top side is mounted on top of the plate 242. It is formed of a suitable material such as a transparent plastic. It is secured to the plate 242 by a flanged bulkhead fitting 247 which extends through the bottom wall of the canister 246 and engages the top surface of the bottom wall. A retainer cap 248 is threaded onto the fitting 247 and engages the bottom side of the plate 242.

A master shaft 249 extends through the flanged bulkhead fitting 247 and the retainer cap 248 for slidable movement. Means is provided within the flanged fitting 247 for forming a floating type bearing seal between the shaft 249 and the fitting 247 and consists of an annular floating bearing seal 251 formed of a suitable material such as Teflon which forms a sealing engagement with the shaft 249. The bearing seal 251 is loosely mounted within a well 252 provided in the fitting 247. An O-ring 253 is mounted in an annular recess 254 provided in the bearing seal 251 and frictionally engages the side wall forming the well 252 to establish a seal between the bearing seal 251 and the fitting 247. This floating bearing seal self-aligns itself with respect to the master shaft 249 and prevents binding between the master shaft 249 and the bearing seal.

Figure 8:
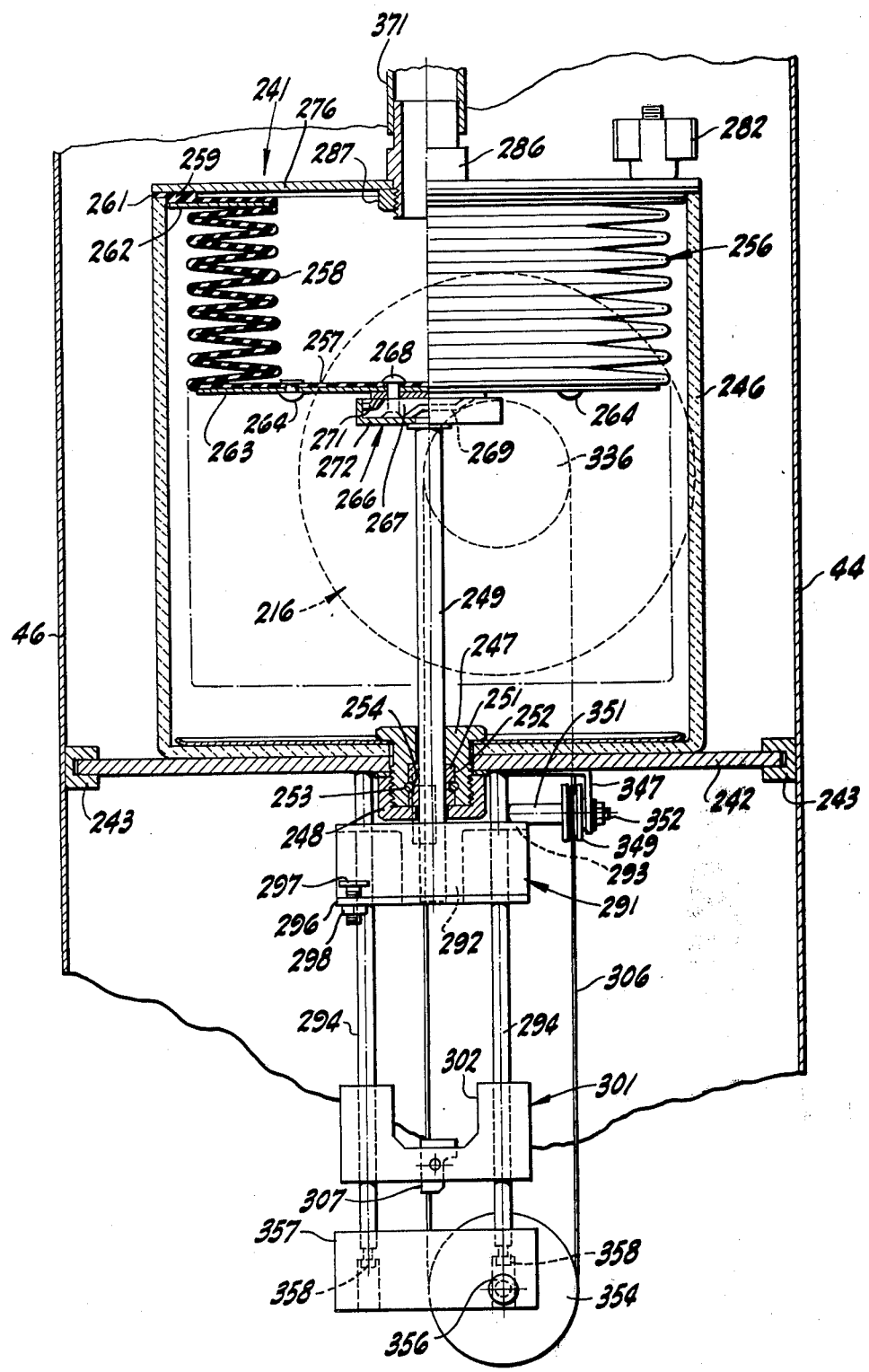
FIG. 8 is a cross-sectional view taken along the line 8—8 of FIG. 7.

The bellows assembly 241 also includes a 2400 c.c. convoluted bellows 256 which is generally cylindrical in form with one end open and formed of a suitable material such as rubber. As can be seen from FIG. 8, the bellows 256 is provided with a flat bottom wall 257 which closes the bottom end of the bellows and a convoluted circular side wall 258 which is adapted to be extended and collapsed to permit movement of the bottom wall of the bellows 256 between collapsed and extended positions as hereinafter described. The bellows 256 is also provided with a rim 259 which carries an annular flange or lip 261 that overlies the upper extremity of the canister 246. An annular plate 262 underlies the rim 259 of the bellows 256 and is of such size so that it can fit within the canister 246. A circular plate 263 is secured to a bottom wall 257 of the bellows 256 by suitable means such as rivets 264.

Quick release connecting means 266 is provided for securing the bottom wall of the bellows 256 to the top of the master shaft 249 and consists of a member or cam pad 267 secured to the bellows 256 and the circular plate 263 by screws 268. The member 267 is provided with clockwise cam threads 269 which are adapted to engage ears or matching threads 271 provided on a mating cup-shaped member or cap 272 secured to the upper end of the master shaft 249 and retained thereon by retaining ring 250. The cup-shaped member 272 and the member 267 can be formed of a suitable material such as plastic. The quick release connecting means 266 provided is in the form of a cam lock which permits the bellows 256 to be readily removed and inserted from the canister 246 by merely rotating the bellows through a relatively small angle for frequent mandated aseptic procedures.

Means is provided for establishing a sealing engagement between the upper end of the canister 246 and the bellows 256 and consists of a cover plate or bellows retention plate 276 of a size which is adapted to cover the top of the canister 246. The cover plate 276 is provided with four outwardly extending ears 277 spaced 90° apart having slots 278 therein adapted to be moved into engagement with the upper ends of four spaced support or caging rods 279 mounted on the plate 242 exterior of the canister 246. The rods 279 are secured to the plate 242 by screws 281. Wing nuts or retention knobs 282 are threaded onto the upper end of the rods 279 and are adapted to engage the ears 277 of the cover plate 276 to hold the cover plate in place and to retain the bellows 256 within the canister 246. The cover plate 276 is provided with a pair of handles 283 to facilitate the rotation of the cover plate 276 in lifting of the same off of the canister 246. A fitting 286 is mounted in the center of the cover plate 276 and is secured thereto by a nut 287 threaded onto the fitting. The fitting 286 is provided with a hole (not shown) to permit gases to enter into the bellows 256 as hereinafter described. Similarly, the canister 246 is provided with a fitting 288 to permit gases to enter the canister 246.

The master shaft 249 follows the movement of the bottom wall of the bellows 256 and has a master cam member 291 secured to the bottom end of the same by suitable means such as a pin (not shown) which also prevents relative rotation between the same. The master shaft 249 transfers all travel of the bottom wall of the bellows 256 proportionally to the master cam member 291. The master cam member as hereinafter described limits bellows travel during intensive care and anesthesia procedures. The master cam member 291 is provided with a central body 292 which receives the master shaft 249. It is also provided with a pair of outwardly extending ears 293 which are slidably mounted on a pair of spaced parallel guide rods 294 that are secured to the plate 242. The master cam member 291 is also provided with a lip 296 which extends outwardly from the body 292 and lies in a plane generally parallel to the ears 293. A headed cam member 297 is mounted upon the lip 296 and is secured thereto by a nut 298 threaded onto the member 297 (see FIG. 7). The headed cam member 297 is adapted to engage an inspiratory volume limiting switch 299 which is secured to the bottom side of the plate 242.

A volume limiting stop member 301 is slidably mounted upon the rods 294. The member 301 is provided with a centrally disposed upwardly facing recess 302 which is adapted to receive the body 292 of the master cam member 291. The master cam member 291 is provided with a pair of recesses 303 which are adapted to accommodate the member 301 when the body 292 seats within the recess 303 so that the ears 293 are adapted to engage the upper extremities of the member 301 and to be moved upwardly as the member 301 is moved upwardly. The members 291 and 301 are formed of a suitable material such as DELRIN (registered trademark) to facilitate sliding movement on the metal rods 294.

Means is provided for moving the stop member 301 vertically of the rods 294 and consists of a suitable flexible elongate element 306 such as a wire cable which is secured to the member 301 in a suitable manner such as by securing the same to a member 307 carried by the stop member 301. As can be seen in FIG. 7, the flexible element 306 extends through the member 307 and is secured thereto by suitable means such as a screw (not shown).

Means is provided for moving the flexible element 306 in the form of the compound knob assembly 216. The compound know assembly 216 consists of a capstan axle 311 which is rotatably mounted in the hub 312. The hub 312 extends through an opening 310 provided in the wall 43 (see FIG. 10). The hub 312 also extends through a mounting plate 314 and is secured thereto by a nut 313 threaded onto the hub 312. The mounting plate 314 is secured to blocks 315 which are mounted upon the two spaced parallel rods 279 adjacent the front wall 43 and are secured thereto by set screws 320. A tidal volume index wheel or knob 316 is mounted on the shaft 311 and is keyed thereto by a key 317 so that as the knob 316 is rotated, the shaft 311 is rotated. The knob 316 is provided with an O-ring 318 mounted in an annular recess 320 of the knob 316. The O-ring 318 engages the outer face of the hub 312 and serves to prevent rotation of the knob 316 when the O-ring 318 is frictionally urged into engagement with the hub 312 under the force of a locking knob 321 which is threaded on the outer end of the shaft 311 and which is retained thereon by a snap ring 322. Thus, when the knob 321 is rotated in a counterclockwise direction as viewed in FIG. 1, the knob 316 is released to permit rotation of the same. When the knob 321 is rotated in a clockwise direction, the knob 316 moves towards the O-ring 318 into engagement with the hub 312 to prevent further rotation of knob 316.

An inspiratory time index wheel or knob 326 is rotatably mounted upon the hub 312. Means is provided for frictionally retarding such rotational movement and consists of a pair of O-rings 327 mounted in annular recesses 328 provided in the hub 312. An internal compliance index wheel 329 is also rotatably mounted on the hub 312. It is also provided with means for frictionally restraining rotational movement consisting of O-rings 331 mounted in annular recesses 332 in the hub 312. The knobs or wheels 326 and 329 are provided with outwardly extending members or handles 333 and 334 respectively which are adapted to be engaged by the hand to facilitate rotation of the knobs 326 and 329. As can be seen from FIG. 14, the members 333 and 334 are threaded into the knobs or wheels and extend radially outwardly therefrom. The knob 316 is calibrated from zero to 2000 whereas the knob 326 is calibrated from zero to 5 and the knob 329 is calibrated from zero to 100. As hereinafter described, the compound control knob serves as a volume delivery computer.

The shaft 311 which forms a part of the compound knob assembly 216 has mounted thereon a pulley or capstan 336 that has a hub 337. Means is provided for causing frictional engagement between the hub 337 and the hub 312 and consists of an O-ring 338 mounted in an annular recess 339 provided in the hub 312. A set screw 341 is provided for securing the capstan 336 to the axle or shaft 311.

Both ends of the flexible elongate element 306 are secured to the pulley or capstan 336. From the pulley or capstan 336, the flexible elongate element 306 extends downwardly over a pair of spaced parallel idler pulleys 343 carried by a sleeve (not shown) rotatably mounted upon a shaft 346 carried by a U-shaped bracket 347 secured to the bottom of the plate 242. The flexible elongate element 306 then travels over another pair of pulleys 349 carried by a sleeve 351 rotatably mounted upon another shaft 352 carried by the U-shaped bracked 347. The flexible elongate element 306 extends downwardly from the pulleys 349. One side extends through the member 307 and is secured thereto. The flexible elongate element 306 then travels over a pulley 354 which is rotatably mounted upon a shaft 356 mounted upon a block 357 carried by and secured to the lower extremities of the rods 294. Thus, it can be seen when the knob 316 is rotated the flexible elongate element or cable 306 will travel over the pulley 354 to cause vertical movement of the member 307 and the volume limiting stop member 301 which serves to define the base line for the volume of gas to be delivered.

Figure 12:
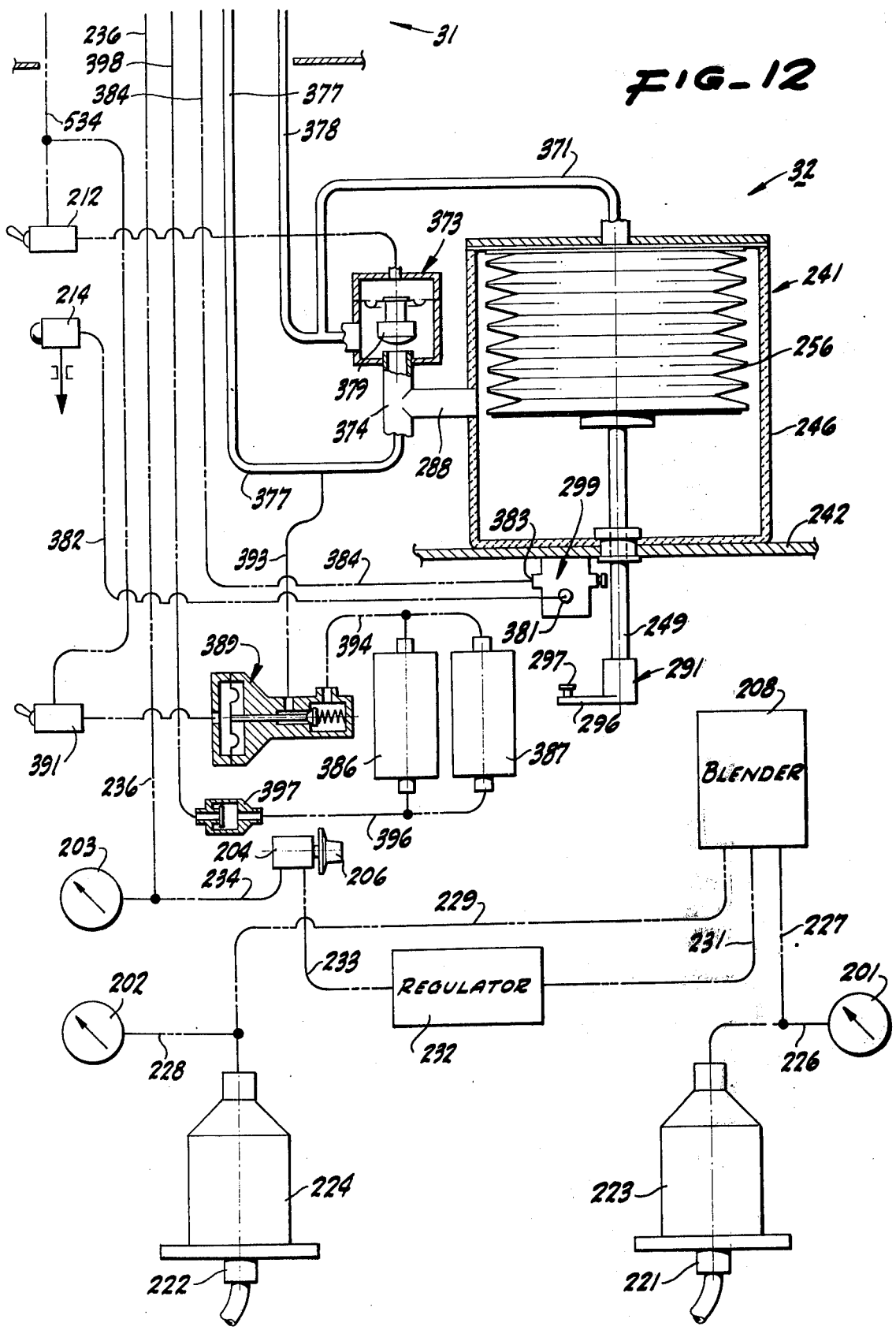
FIG. 12 is an illustration largely schematic of the parts and the conduits provided in the lower cabinet or module of the respirator.

Means is provided for establishing communication with the canister 246 and the bellows 256 and consists of a large tube 371 which has one end secured to the fitting 286 provided in the cover plate 276. The other end of the tube 371 is connected to a tee 372 (see FIG. 3). One leg of the tee 372 is mounted in an inspiratory transfer valve assembly 373. The other end of the valve assembly 373 is mounted in one end of a tee 374. Another leg of the tee 374 is mounted upon the fitting 288 provided on the canister 246. The other leg of the tee 374 is connected to a 90° elbow 376. A large tube 377 has one end connected to the elbow 376 and has its other end extending upwardly into the upper cabinet 31. The other leg of the tee 372 has another large tube 378 connected to the same which also extends upwardly into the cabinet 31. The valve assembly 373 includes a valve member 379 (see FIG. 12) which is a movable under air pressure to prevent gas from flowing into the bellows 256.

The inspiratory termination cartridge 299 has a fitting 381 mounted therein which is connected by a tube 382 to the wink light 214. It is also provided with another fitting 383 which is connected by a tube 384 which extends into the upper cabinet 31 for a purpose hereinafter described.

Figure 3:
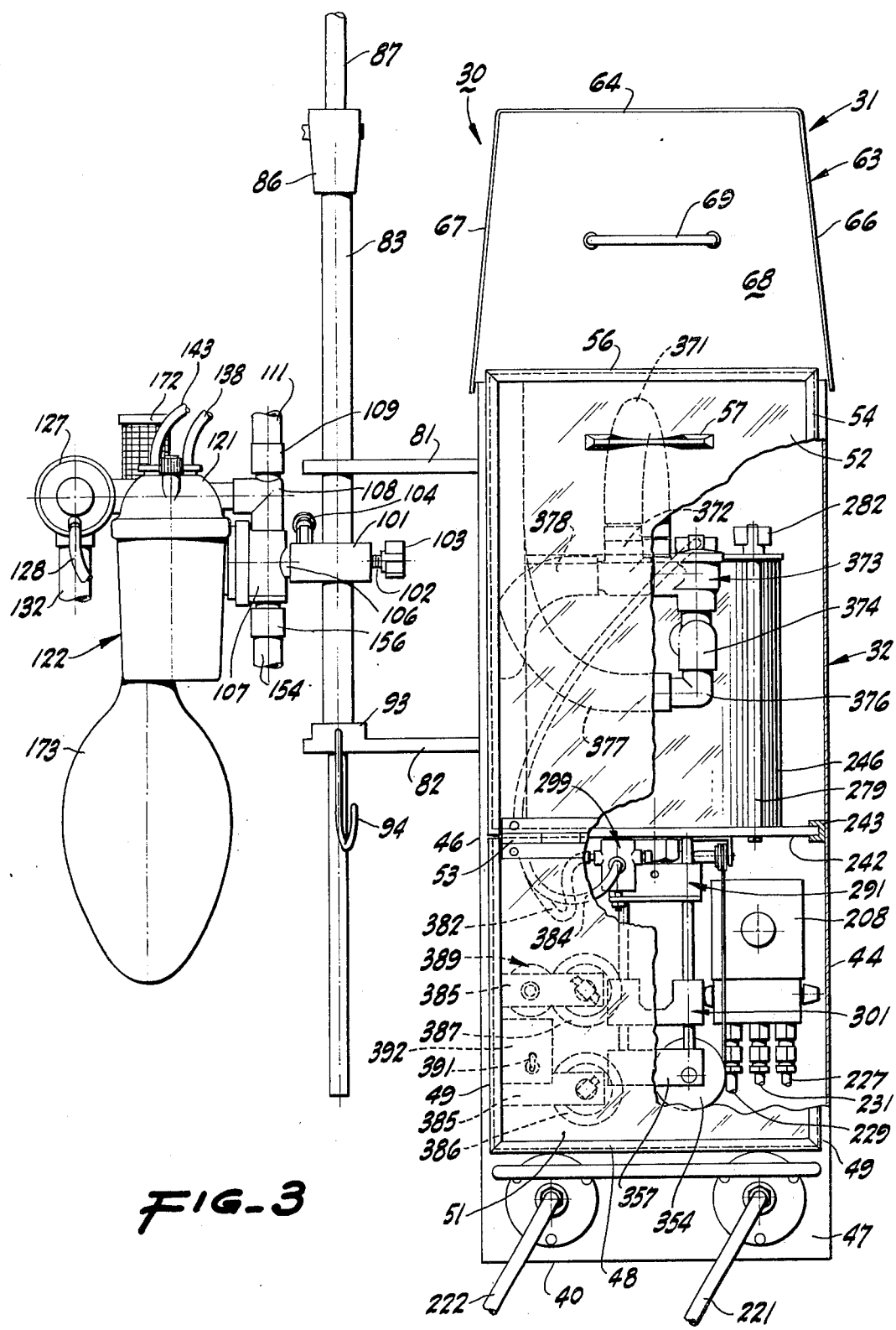
FIG. 3 is an enlarged rear elevational view of a portion of the respirator shown in FIG. 1.

In order to obtain a higher flow rate from the respirator in certain applications, means has been provided to supply supplemental gas. To accomplish this, an accumulator of a suitable size has been provided. Thus, as shown in FIG. 3, there has been provided two 250 cc reservoirs 386 and 387 which are carried by a pair of U-shaped brackets 385 mounted on the side wall 46. A normally closed accumulator discharge cartridge 389 is also mounted on the bracket 385. A toggle switch 391 is mounted upon a bracket 392 which is also mounted upon the side wall 46. One side of the normally closed accumulator discharge cartridge 389 is connected by a tube 393 to the tube 377. The other side of the cartridge 389 is connected by a tube 394 to one side of both of the accumulators 386 and 387. The other ends of the accumulators 386 and 387 are connected by a tube 396 to one side of a one-way check valve 397. The other side of the check valve 397 is connected to a tube 398 which extends into the upper cabinet or module 31.

Returning now to the upper cabinet 31, there is provided a large generally vertical mounting plate 401 formed of a suitable material such as plastic which is secured by screws 402 to three mounting posts 403. The mounting posts 403 extend upwardly from the front panel 61 and are secured thereto by screws 404. A plurality of cartridges as hereinafter described are mounted on the mounting board 401. Thus on the front side of the mounting plate 401 in a top row there is provided an expiratory flow cartridge 406 and an apneustic plateau cartridge 407. The cartridges 406 and 407 and the other cartridges hereinafter described are all mounted on the mounting plate 401 in a suitable manner such as by each having a boss extending through a hole provided in the mounting plate and then having a retaining ring snapped over the boss to retain the cartridge in the mounting plate. A manifold (not shown) is mounted in the expiratory flow cartridge 406. Similarly, a manifold 412 is provided in the apneustic plateau cartridge 407.

In a second or middle row on the front side of the mounting plate 401 there is provided an inspiratory termination cartridge 416. There is also provided an expiratory flow gradient delay cartridge 417. An expiratory termination cartridge 418 is mounted below the expiratory flow gradient delay cartridge on the front side of the mounting plate 401.

On the back side of the mounting plate 401 there is provided what is called a peep termination cartridge 421. Also provided on the back side of the mounting plate 401 is an auto sensitivity cartridge 422 and a demand flow accelerator cartridge 423. An adjustable orifice 424 is also mounted on the mounting plate. An inspiratory flow acclerator cartridge 426 is also mounted in a top row of the back side of the mounting plate 401. An IMV control cartridge 427 and a reservoir demand flow accelerator cartridge 428 are mounted in a middle or second row on the back side of the mounting plate 401. Also included in the middle row is an IMV assist cartridge 429. A large hole 431 is provided in the mounting plate to obtain access to the rear side of the sequencing servo 188 which is mounted on the front panel 61. A fail safe cartridge 432 is mounted in a bottom row on the rear side of the mounting plate 401. A pair of manifolds 433 and 434 are mounted on the rear side of the mounting plate 401.

A metal bracket 441 is secured to the breathing tube receptacle 113 and to the front panel 61 and extends rearwardly and underlies the lower extremity of the mounting plate 401. Another bracket 442 is secured to the bracket 441 and is also secured to the lower extremity of the mounting plate 401 to provide a support for one corner of the mounting plate 401.

The breathing tube receptacle 113 is connected to one leg of a tee 446 mounted in the upper cabinet 31. Another leg of the tee 446 is connected to the leg of another tee 447. Another leg of the tee 447 is connected to a one-way flapper check valve assembly 448 which only permits flow in the direction indicated by the arrow 449. The check valve assembly 448 is connected to the large tube 378 which extends downwardly into the lower cabinet 32. An over pressure governor assembly 451 is mounted in the remaining leg of the tee 447. An audio alarm assembly 452 is mounted on the over pressure governor assembly 451.

Another tee 457 has one leg of the same mounted in The remaining leg of the tee 446. However, the leg of the tee 457 which is mounted in the tee 446 is provided with a plug 458 which prevents the passage of gas from the tee 446 into the tee 457. A sensing-servoing venturi assembly 461 is mounted in one leg of the tee 457. Another tee 462 is mounted in the remaining leg of the tee 457. A master venturi assembly 463 is mounted in the leg of the tee 462. Another tee 464 is mounted in the remaining leg of the tee 462. An over pressure governor 466 is mounted in one leg of the tee 464. An inspiratory termination valve assembly 467 is mounted in the remaining leg of the tee 464. The inspiratory termination valve assembly 467 is connected to the large tube 377 extending into the lower cabinet 32. A U-bolt 469 extends around the tee 462 and is secured to the bracket 441 and provides a support for the assembly hereinbefore described so that it will not be accidentally broken off of the breathing tube receptacle 113. A tee-shaped flapper valve assembly 471 is mounted on the master venturi assembly 463. The tee-shaped flapper valve assembly is provided with two flapper valves 472 and 473. The flapper valve assembly 471 is supported by a support member 476 which is carried by a rod 477 secured to the front panel 61. An inlet filter 478 is mounted in one of the legs of the tee-shaped flapper valve assembly 471 and provides an inspiratory saftey inlet to ambient air.

A tee 481 is mounted in the other leg of the tee-shaped flapper valve assembly 471. An over-pressure governor assembly 482 is mounted in one leg of the tee 481. An entrainment reservoir 483 is connected to the other leg of the tee 481.

A pair of adjustable orifices 486 and 487 are mounted on the bracket 488 provided for mounting the manometer 186. An auxiliary reservoir 491 formed of a suitable material such as plastic and in the form of a cylinder is secured to one of the support posts 403 by plastic bands 492.

The details of the various cartridges and other components utilized in the apparatus hereinbefore described have been described in detail in earlier filed copending applications. Thus, the expiratory flow gradient delay cartridge 417, the expiratory termination cartridge 418, the expiratory flow cartridge 406, the inspiratory termination cartridge 416 and the fail-safe lock-out cartridges 432 are all of the normally open type and are of the type disclosed in FIG. 9 of copending application Ser. No. 544,505, filed Jan. 27, 1975 now U.S. Pat. No. 3,974,828. The peep termination cartridge 421, the IMV assist cartridge 429 and the IMV control cartridge 427 are all of the normally closed type and can be the type shown in FIG. 12 of copending application Ser. No. 499,554, filed Aug. 22, 1974 now U.S. Pat. No. 3,915,164.

The I.M.V. on-off switch 183 is a switch of the type supplied by Humphrey of Kalamazoo, Michigan. The I.M.V. demand flow accelerator cartridge 423, the reservoir demand flow accelerator cartridge 428 and the autosensitivity cartridge 422 are all of the type disclosed in FIG. 6 of copending application Ser. No. 544,505, filed Jan. 27, 1975 now U.S. Pat. No. 3,974,828. The sequencing servo 188 is of the type disclosed in FIG. 7 of copending application Ser. No. 499,554 filed Aug. 22, 1974 now U.S. Pat. No. 3,974,828.

Figure 4:
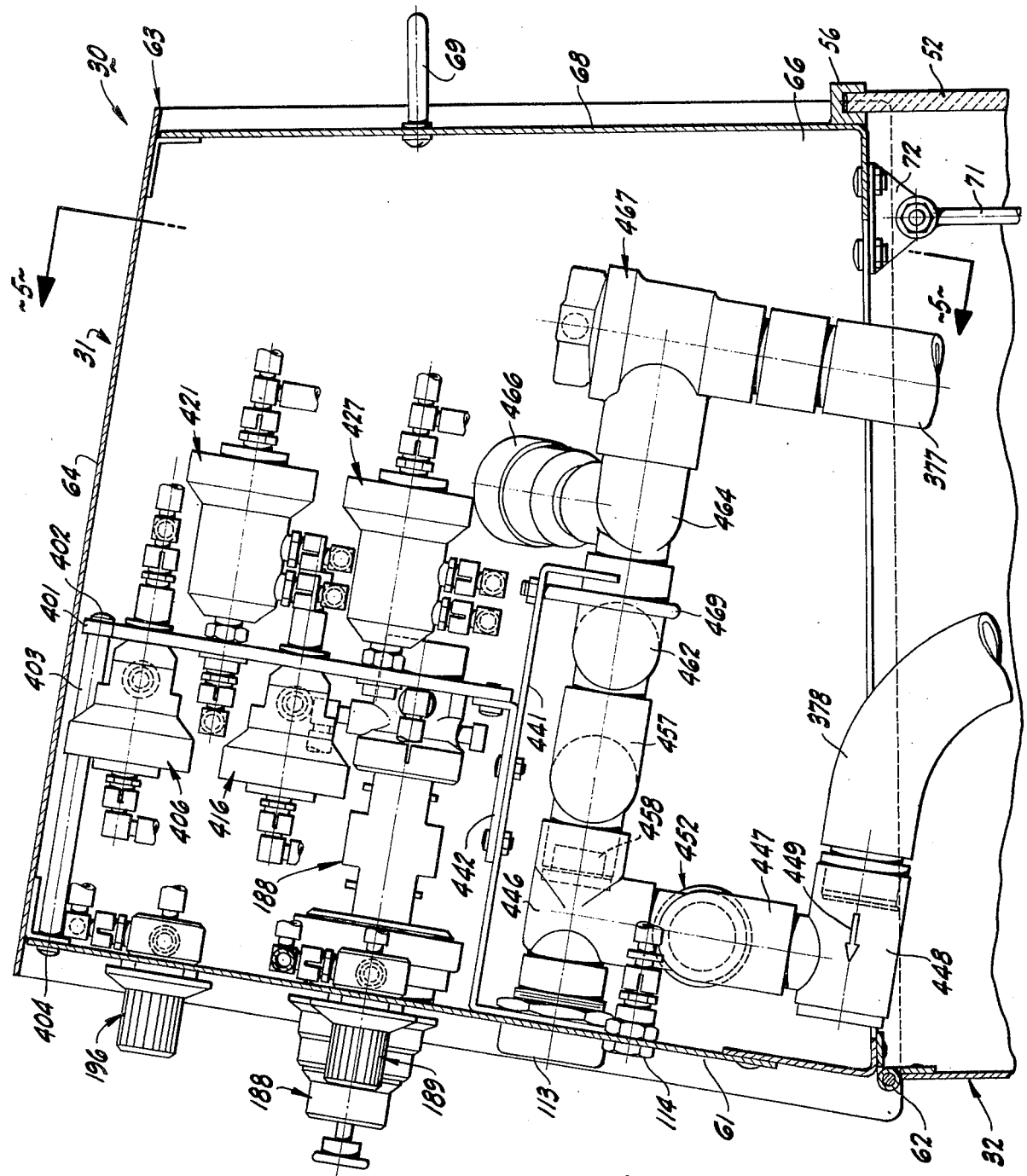
FIG. 4 is a cross-sectional view taken along the line 4—4 of FIG. 2.
Figure 10:
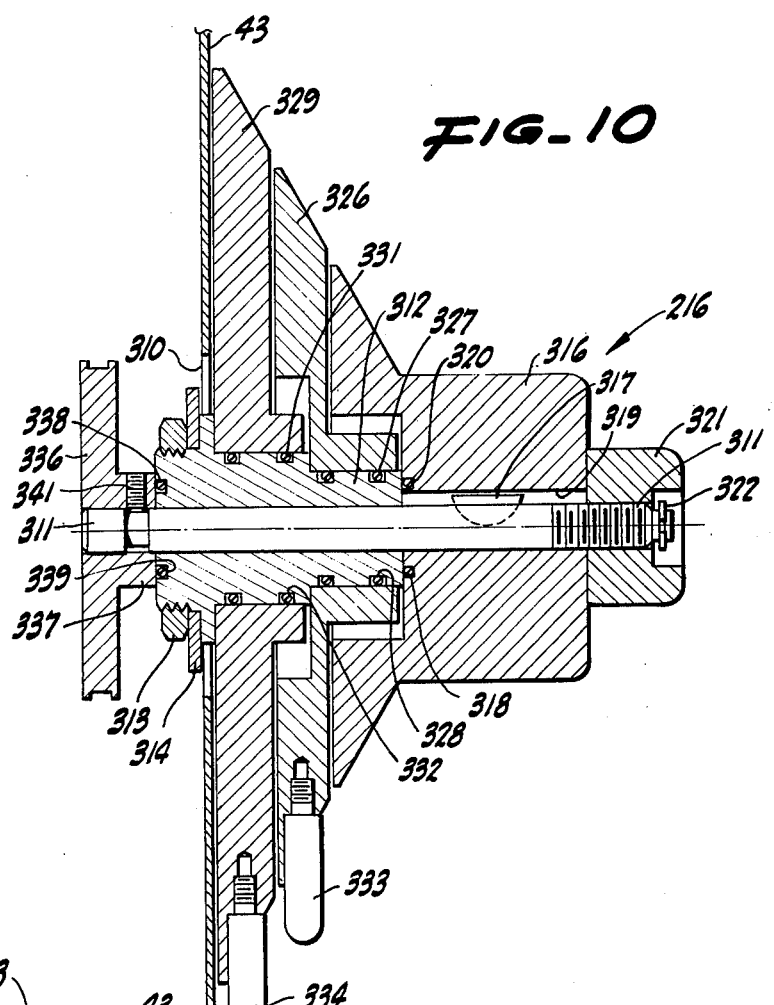
FIG. 10 is an enlarged cross-sectional view of the compound dial assembly provided in the lower cabinet or module.
Figure 11:
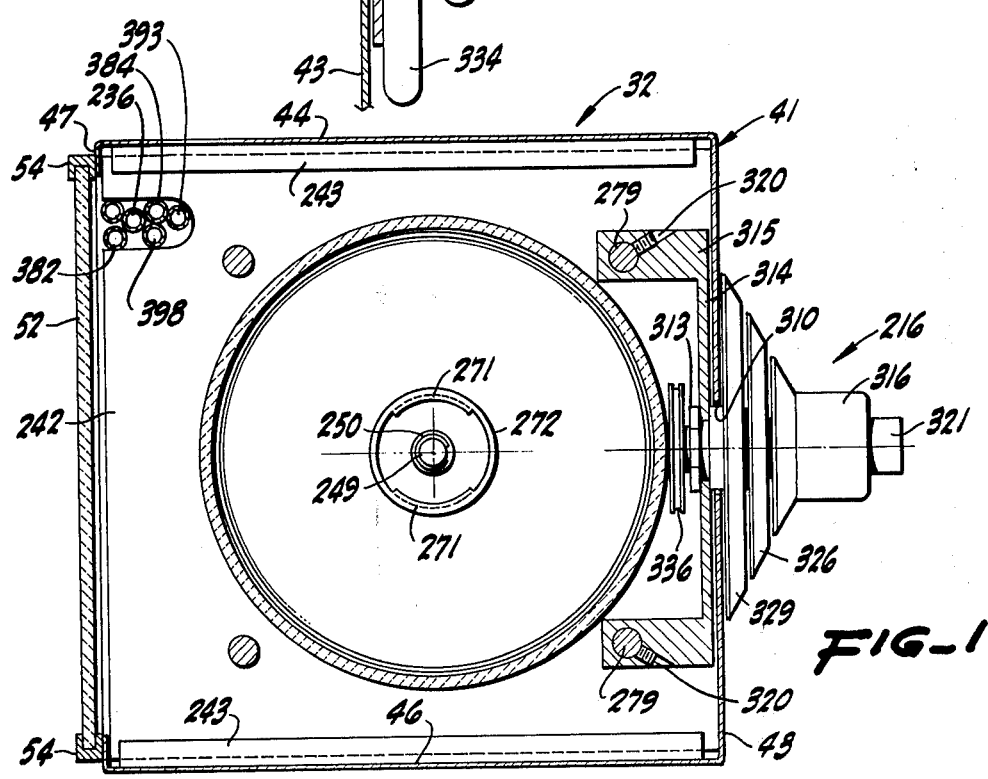
FIG. 11 is a cross-sectional view taken along the line 11—11 of FIG. 7.

The alarm assembly 452 is ot the type disclosed in FIGS. 9, 10 and 11 of U.S. Pat. No. 3,842,828. The flapper valve assembly 471 is of the type disclosed in FIG. 4 of copending application Ser. No. 544,505, filed Jan. 27, 1975 now U.S. Pat. No. 3,974,828. The entrainment reservoir 483 is like the entrainment reservoir 174 shown in FIG. 3 of copending application Ser. No. 544,505, filed Jan. 27, 1975 now U.S. Pat. No. 3,974,828. The overflow relief valve 482 and the over-pressure governors 451 and 446 are like the over-pressure governor 158 shown in FIG. 4 of copending application Ser. No. 544,505, filed Jan. 27, 1975 now U.S. Pat. No. 3,974,828. The sensing venturi assembly 461 is like the sensing venturi assembly 216 shown in FIG. 5 and the master venturi assembly 463 is like the venturi assembly 181 also shown in FIG. 5 of copending application Ser. No. 544,505, filed Jan. 27, 1975 now U.S. Pat. No. 3,974,828. The adjustable orifices and check valves which are shown in the schematic flow diagram are of a conventional type.

GENERAL OPERATION

Figure 2:
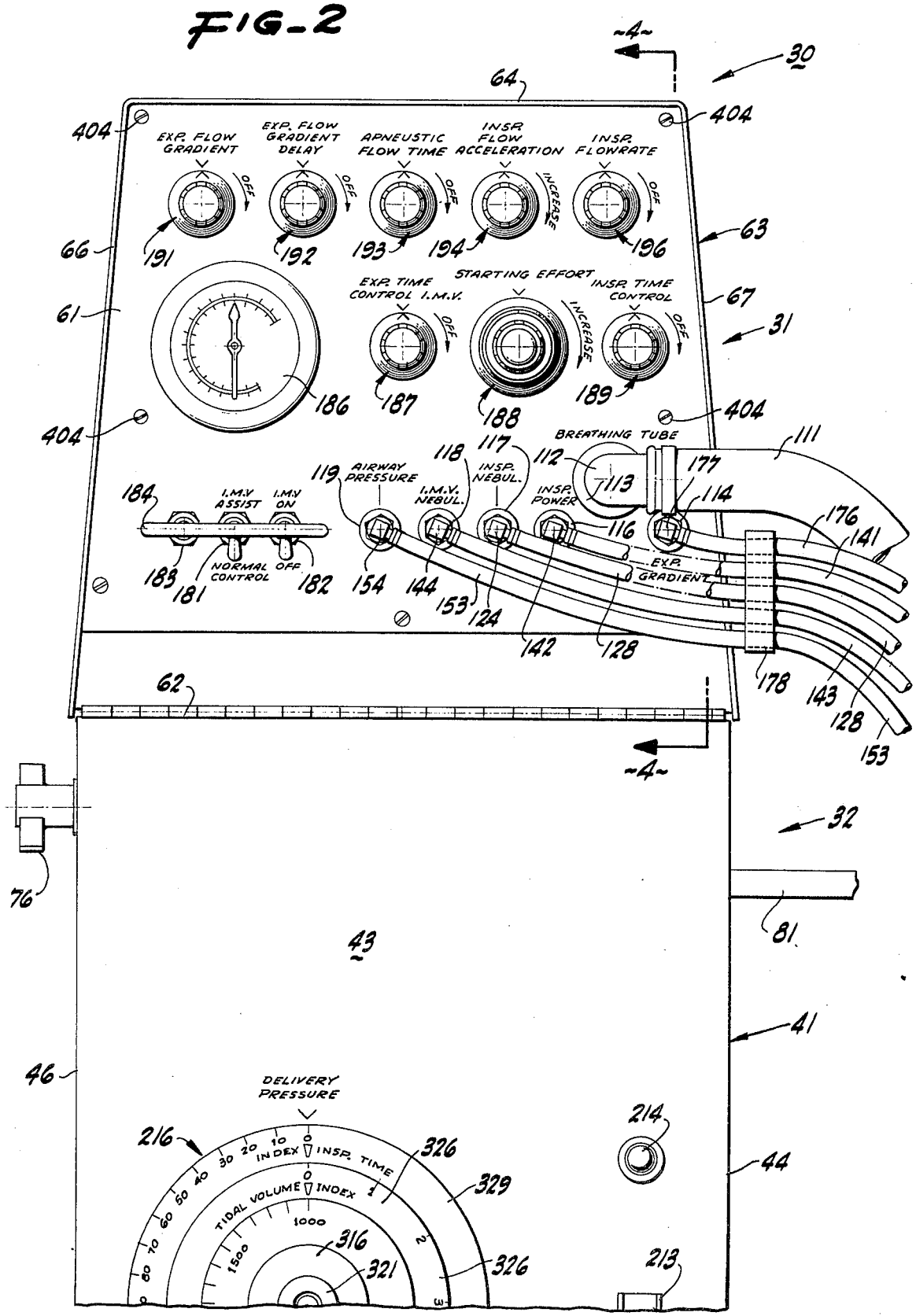
FIG. 2 is an enlarged front elevational view of a portion of the respirator shown in FIG. 1.

Operation of the respirator or ventilator 30 may now be briefly described as follows. Let it be assumed that it is desired to ventilate a patient with the respirator and that it is desired to adjust the controls of the respirator for the particular patient. First, the compound knob assembly 216 can be adjusted so that all of the dials are in the 12 o'clock position as shown in FIG. 2. The IMV toggle switch 182 will be in a down or off position and the IMV assist toggle switch 181 will also be in the down or normal control position as viewed in FIG. 2. The starting effort is then adjusted by adjusting the control knob on the sequencing servo 188 to a servo value as, for example, a −2 which represents a −2 cm of water pressure. The peak starting pressure is also adjusted on the sequencing servo assembly 188 to a suitable value as, for example, 60mm of mercury by adjusting the appropriate dial to the value of 60. The upper cabinet or module 31 is now set.

Now going to the lower cabinet or module 32, let it be assumed that it is desired to operate the respirator in the volume limiting mode. When this is the case, the toggle switch 212 is moved to the up position.

Let it be assumed that the patient requires intensive care. The tidal volume for the patient must then be selected. Let it be assumed that it is desired to utilize a volume of 1 liter or 1000 cc. The locking knob 321 is loosened and the tidal volume dial or wheel 316 is adjusted to the 1000 cc position as shown in FIG. 2 after which the locking knob 321 is then tightened. In this manner the position of the base line for volume limiting has been established by adjusting the position of the stop member 301.

The gauges 201 and 202 are then checked to ascertain whether or not the air and oxygen pressures are adequate for operation of the respirator. The control knob 211 on the blender 208 is then adjusted to a suitable value as, for example, to a value of 40% giving the mixed gas a 40% concentration of oxygen.

As soon as these steps have been accomplished, the respirator may be placed in operation. Let it be assumed that the respirator has been connected to the airway of the patient in a suitable manner that is, for example, by the use of the patient adapter 152. The respirator can then be turned on by operating the master on-off switch 204 to place it in the on position. Thereafter, the operating pressure is determined by examining the indication given by the operating pressure gauge 202. At the same time, the wink light 214 is examined to ascertain whether or not it is periodically flashing a green color which signals mechanical completion of delivery of a predetermined volume to the airways of the patient. The patient's chest is then examined to be sure that it is moving up and down under control of the respirator.

Let it also be assumed that all of the other control knobs provided in the upper cabinet or module 31 are in their 12 o'clock positions. After the respirator has been placed in operation, let it be assumed that it is desired to make certain adjustments to the ventilatory procedures which are occurring. When the respirator is in the volume limiting mode, the 12 o'clock position for the control knob of the inspiratory flow rate control assembly 196 should be satisfactory. However, let it be assumed that for the particular patient, the lungs of the patient are not being inflated as fast as desired. To accomplish a more rapid inflation, the inspiratory time must be decreased. This is accomplished by turning the knob of the inspiratory flow rate assembly 196 in a counter-clockwise direction which causes earlier commencement of the inspiratory phase.

The apneustic flow time control assembly 193 can be adjusted. If minimal apneustic flow time is desired, the control knob of the assembly 193 is adjusted to a minimum which would be less than a quarter of a second, whereas if a full apneustic flow time is desired, the control knob of the assembly 193 is rotated to the other extreme position to give a maximum apneustic flow time as, for example, 3 seconds. As hereinafter described, when apneustic flow is utilized, 200 cc per second can be delivered to the patient's lungs.

Now let it be assumed that it is desired to adjust the constant positive airway pressure, hereinafter called CPAP. For the time being, the control knob of the expiratory flow gradient delay assembly 192 is left in the 12 o'clock position. The control knob of the expiratory flow gradient control assembly 191 is adjusted to a minimum position. The manometer 186 is then observed to ascertain the expiratory flow gradient during the expiratory phase which by way of example, can be approximately 5 cm of water pressure. In other words, with a CPAP at such a minimum value, the patient would be exhaling against the positive pressure above atmospheric corresponding to 5 cm of water rather than zero. Let it be assumed by way of example that it is desired to ahve the patient exhale against a pressure corresponding to 10 cm of water. The control knob of the expiratory flow gradient control assembly 191 is adjusted until one observes a value of 10 on the manometer 186 during the expiratory phase. In other words, at the end of the expiratory flow, the indicator of the manometer 186 should be resting at the position representing 10 cm of water.

By adjusting the control knob on the expiratory flow gradient delay control assembly 192, the application or start of CPAP can be delayed so that it can be near the end of the expiratory phase. In this way it is possible to provide a true positive and expiratory pressure, hereinafter PEEP. This makes it possible for the patient to exhale most of his air to the atmosphere at a low pressure before the application of an expiratory pressure against which he must exhale. By the use of two of these two control assemblies 191 and 192, it is possible to obtain CPAP and PEEP over a wide range during the expiratory phase.

In connection with the foregoing, it has been assumed that the patient has been breathing spontaneously. As hereinafter described, as soon as the patient drops the pressure in the breathing circuit to below −2 cm of water pressure as set up by the starting effort dial on the sequencing servo 188, the respirator will immediately enter the inspiratory phase because the respirator, as hereinafter explained, is provided with automatic sensing means which will turn the respirators on when such a condition occurs.

Now let it be assumed that the patient has stopped breathing spontaneously, and it is desired to control the breathing rate of the patient. This is controlled in the conventional manner by the expiratory time control assembly 187 which, as hereinafter described, causes the respirator to switch to the inspiratory phase after it has been in the expiratory phase for a predetermined period of time. Similarly, the inspiratory time ca be adjusted by adjustment of the control knob of the inspiratory time control assembly 189. By way of example, when the patient has stopped breathing spontaneously, let it be assumed that the control knobs of the assemblies 187 and 189 have been adjusted so that there is a 3 sec. inspiratory time and a 4½ sec. expiratory time, giving a ratio of 1:1.5. However, in this connection, it should be recalled that the respirator could be cycled either by the patient obtaining 1 liter of gas as determined by the setting of the compound knob assembly 216, or by the pressure corresponding to 60 cm of water being established in the patient's airways or by the elapsed time as established by the inspiratory time control valve assembly 189 depending upon which came first.

In connection with the concept of delivering 1 liter of gas to the patient, it should be recalled that in the respirator, as herein described, many of the parts of the respirator through which the air under pressure to the patient must pass have compliance. In other words, they will distend under pressure. For example, the bellows 256 which is formed of rubber will stretch, as will the large tubes or hoses 132 and 136 carrying the gas under pressure to the patient. Also, it should be appreciated that the higher the pressure, the more the yield factor in the various parts. This is also true of the lungs of the patient which have compliance. The compound knob assembly 216 forms a computer for compensating for such characteristics. To utilize the compound knob assembly 216, one examines the manometer 186 and by way of example finds that it requires 40 mm of mercury to deliver 1000 cc of gas to the patient upon each delivery. The control knob of wheel 329 is then adjusted until the number 40 is in the 12 o'clock position.

In the present respirator, it is known that the two nebulizers 122 and 127 are delivering 200 cc of additional gases into the airways of the patient for the purposes of nebulizing and humidifying the gases. Since this would represent an error in the 1000 cc to be delivered to the patient, the control knob of wheel 326 is adjusted in a counter-clockwise direction as viewed in FIG. 2 until the appropriate number representing expiratory time, as for example, 3½ seconds, underlies the inspiratory time index carried on the wheel or dial 329. In this connection, it has been assumed that the inspiratory time is 3 sec. and that the apneustic plateau time is one-half second. After this has been accomplished, the tidal volume dial or knob 316 is rotated so that the number 1000 representing 1000 cc's underlies the tidal volume index indicia carried by the dial or wheel 326. As soon as all this has been accomplished, the lock knob 321 can be rotated to lock the dials or wheels into the positions in which they have been moved.

By making the type of adjustments hereinbefore described of the compound knob assembly 216, it can be seen that the various variables which would constitute significant factors in ascertaining whether or not 1000 cc of gases are delivered to the airways of the patient have been taken into account by rotating the wheels or dials 329, 326 and 316 to the positions indicated. This would mean that substantially precisely 1000 cc of gases would be delivered to the patient during the time that the respirator is in the volume limiting mode. However, it should be appreciated that if the maximum inspiratory pressure which has been set into the sequencing servo 188 is reached first, the respirator will be cycled by the maximum pressure rather than by volume limiting. In this connection, it should be appreciated that normally the pressure would be set at high enough values so that when volume limiting is desired, this would be the mode in which the respirator would operate, and it is only in an emergency situation that pressure limting would occur as a back-up. However, if desired, the pressure could be set at a low enough value so that pressure limiting and/or volume limiting would occur at approximately the same time. For example, this could be accomplished by setting the pressure limiting at 40 switch is approximately the pressure which is developed in delivering 1000 cc of gas to the patient.

Now let it be assumed that the patient has again resumed breathing spontaneously, and that he is breathing ahead of the control rate of the respirator. Let it also be assumed that it is desired to place the patient on intermittent mandatory ventilation. This is accomplished by switching the IMV toggle switch 182 to the up position. As hereinafter explained, this permits the patient to breathe spontaneously. The patient will be able to breathe rather effortlessly and will obtain a gas with a 40% oxygen mixture. However, when the patient is exhaling or breathing out, he will be exhaling against a CPAP of 10 because of the settings previously discussed. As hereinafter explained, the more the control knob is adjusted on the expiratory time control assembly 187, the more breaths the patient can take spontaneously before there is a control back-up provided by the intermittent manditory ventilation. In addition to the two toggle switches 181 and 182, there is provided the metering valve which, for example, after a predetermined period of expiration will automatically dump the expiratory control circuit to ambient. This completes a general discussion of the function of the controls provided on the upper and lower cabinets or modules 31 and 32.

DETAILED OPERATION

Figure 13:
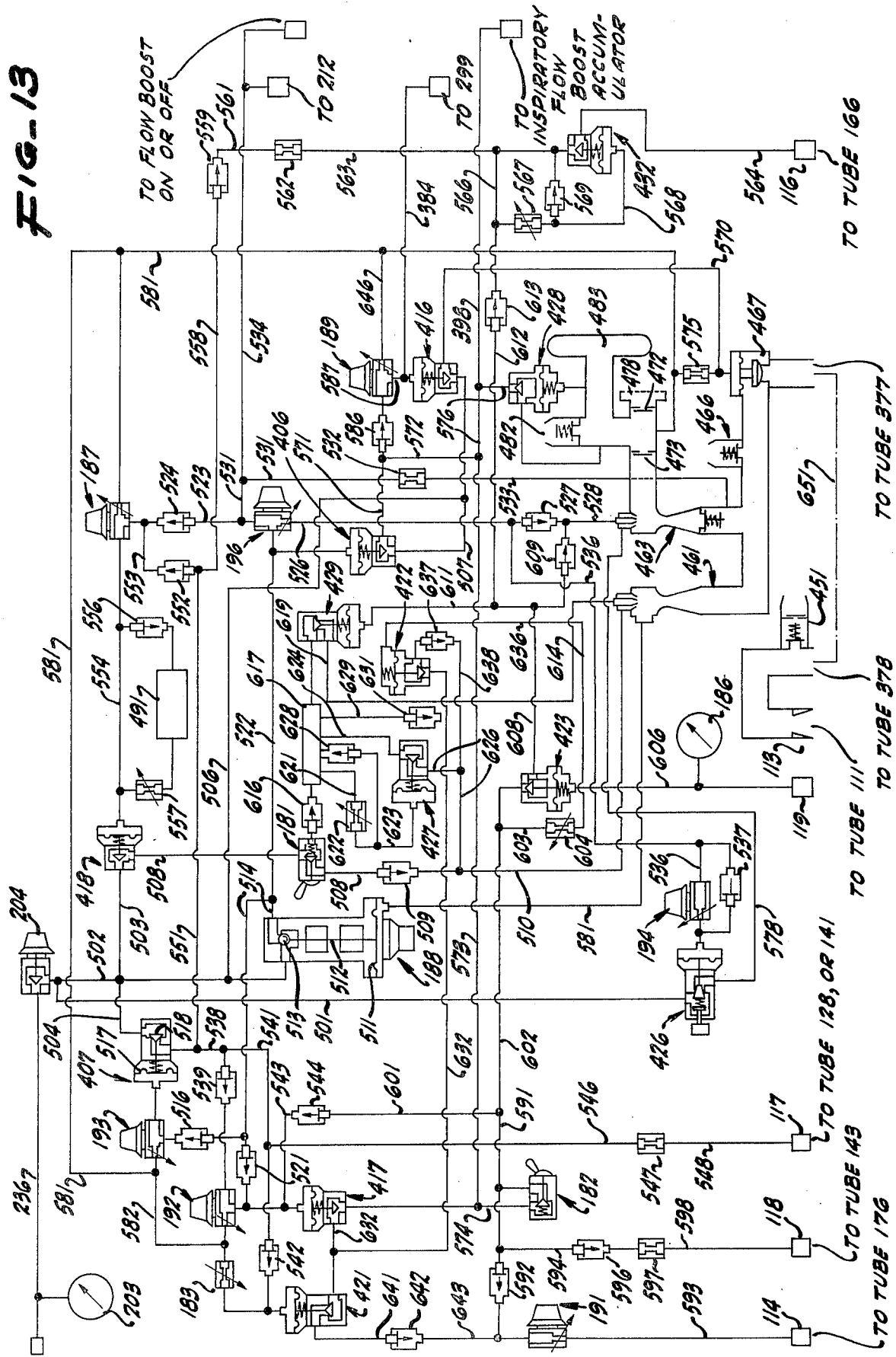
FIG. 13 is a flow diagram schematically illustrating the operation of the parts and components provided in the upper cabinet or module of the respirator with only a few of the components from the lower cabinet or module.

A detailed operation of the respirator may now be described in conjunction with the flow diagram shown in FIG. 13. All of the parts or components shown in FIG. 13 are in the upper cabinet or module 31 with the exception of the source pressure gauge 203 and the master on-off switch 204 which are located in the bottom cabinet or module 32 when the respirator includes such a bottom cabinet or module. Let it be assumed that a gas of the desired mixture as, for example, 40% oxygen at a suitable pressure as, for example, 50 psi is supplied to the source pressure gauge 203 from the regulator 232 and the blender 208 provided in the lower cabinet or module 32 through the line 236 to the on-off switch 204. Let it be assumed that the master on-off switch 204 has been operated to permit source gas to flow through the same. Source gas is then delivered from the master on-off switch 204 through a line 501 to one side of the inspiratory flow accelerator cartridge 426.

It should be understood that the lines hereinafter described in conjunction with the flow diagram shown in FIG. 13 have been simplified for purposes of illustration and do no necessarily correspond exactly to the physical tubular connections provided between the various parts in the respirator. However, one skilled in the art, upon seeing the flow diagram in FIG. 13, would have no difficulty in plumbing the parts in the respirator in the manner shown in FIG. 13.

Source gas is also supplied through a line 502 to the inlet of the sequencing servo 188. This same source gas is supplied by line 503 to one side of the normally open expiratory termination cartridge 418 and by a line 504 to one side of the apneustic plateau cartridge 407. Source gas is also supplied by a line 506 to one side of the inspirator termination cartridge 416. Another line 507 is provided for supplying source gas to one side of the normally open expiratory flow cartridge 406. This represents that total distribution of the source gas in the respirator.

INHALATION PHASE

It should be appreciated that initially when the master on-off switch is turned "on" that source gas will be supplied to line 503 and through the normally opened expiration termination cartridge 418 through line 508 the IMV assist-control selector switch 181. Assuming that the switch 181 is in the down position rather than the up position shown in FIG. 13, the gas will be supplied through the check valve 508 through the line 510 to the outer jets of the sensing venturi assembly 461. This introduction of the gases into the sensing venturi assembly 461 will cause a negative pressure to be created in the sensing venturi which will be sensed by the line 581 and supplied to the diaphragm side of the sequencing servo 188 to move downwardly and to remove the ball 513 to permit source gas to pass therethrough. This will cause the respirator to enter the inspiratory or inhalation phase to cause the sequence of operations hereinafter described.

The sequencing servo 188 operates in a manner described in copending application Ser. No. 544,505, filed Jan. 27, 1975 now U.S. Pat. No. 3,974,828. As described therein, the sequencing servo 188 includes a diaphragm 511 which senses a sub-ambient condition in the patient breathing circuit such as caused by the patient attempting to take a breath and causes movement of the plunger 512 to move the ball valve 513 off of its seat and to permit source gas to flow from the line 502 into a line 514 through a check valve 516 through the apneustic plateau control assembly 193 and then to the apneustic plateau cartridge 407 to load the diaphragm 517 to move the valve 518 to move it to an open position so that apneustic flow can commence. In the event that the apneustic plateau cartridge 407 fails to operate, source gas under pressure is supplied through the interlock check valve 521 to the diaphragm side of the normally open expiratory flow gradient delay cartridge 417. Gas is also supplied to the expiratory flow gradient delay control assembly 192 through the dynamic expiratory termination valve assembly 183 and then to the diaphragm side of the normally closed PEEP termination cartridge 421. However, as hereinafter explained, the apneustic flow normally would arrive first to load the diaphragms of the two cartridges 417 and 421 and also would be of a higher pressure. It is only when the apneustic plateau cartridge fails to deliver apneustic flow that gas would be supplied through the interlock check valve 521 to the cartridges 417 and 421.

Gas is also supplied by the sequencing servo 188 in the inspiratory phase to a line 522 which is connected to the flow rate control valve 196 and supplies gas through a line 523 to one side of an interlock check valve 524. Gas is also supplied through the metering flow rate control assembly 196 to a line 526 through a check valve 527 and then through a line 528 to the master or central jet of the master venturi assembly 463. This is the primary gas flow rate control valve assembly 196. When the respirator is in the volume limiting mode the primary gas flow is into the large tube 377.

Means is provided for bleeding down or scavenging the line 522 leading from the sequencing servo 188 and consists of the line 531 which is connected to the line 523 on the other side of the flow rate control valve assembly and is connected to a restrictied orifice 532. The other side of the orifice 532 is connected by a line 533 to the scavenging side of the master venturi assembly 463 to deliver the same to the breathing circuit for the patient. This path provided through the restricted orifice 532 ensures that gas under pressure will not be locked up in the line 522 and thus ensures that the pressure in the line 522 will always drop to zero during the expiratory phase of the sequencing servo 188.

Gas is also supplied from the line 531 through a line 534 to the volume pressure selector switch 212 in the lower cabinet 32. When the selector switch 212 is in position to permit gas under pressure to flow through the same into the transfer valve assembly 373, the valve member 379 is moved into a closed position to cause the primary flow of gas from the tube 377 to flow into the canister 246 and around the outside of the bellows 256.

As the canister 246 is pressurized, the bellows 256 is moved upwardly to cause the gas carried within the bellows to be forced out through the large tube 371 and up through the large tube 378 into the upper cabinet where it passes through the large fitting 113 into the patient breathing circuit external to the upper cabinet 31 and then into the large tube 111, thence through the 500 cc nebulizer 122 and through the small nebulizer 127 and then through the large tube 132, through the large tube 136, through the swivel unit 146 and into the patient adapter 152 and thence into the lungs of the patient. Raising of the bellows 256 causes raising of the master shaft 249 attached to the bellows which causes raising of the master cam member 291 which is slidably mounted on the guide rods 294. Upward movement of the lower extremity of the bellows 256 continues until the headed cam member 297 carried by the master cam member 291 engages the plunger of the inspiratory volume limiting switch 299. As soon as this occurs, the line 384 is dumped to the atmosphere which causes termination of the inspiratory phase due to volume limiting. This change in pressure will be communicated to the line 382 to the wink light 214 to indicate a change in condition. The line or tube 384 is pressurized with gas during the expiratory phase from source gas from the master on-off control switch 204 through the line 506 and 507 and through the normally open expiratory flow cartridge 406. In the expiratory phase the expiratory flow cartridge 406 is in its normally open position so that source gas is supplied to a line 571 through a check valve 586 and then through the inspiratory time control valve assembly 189 to pressurize the diaphragm side of the normally open inspiratory termination cartridge 416. Gas is also supplied to the line 384 to the inspiratory termination switch 299 and to the wink light 214 through line 382. At the same time gas is supplied from the line 571 to a line 576 which is in communication with the inlet side of the reservoir demand flow accelerator cartridge 428 which may also be called an entrainment reservoir cartridge. The line 576 is connected to the line 398 which is connected to the inspiratory flow boost accumulator chambers 386 and 387 through a check valve 397, all of which are provided in the lower cabinet. The line 572 is also connected to a line 573 which is connected to the inlet side of the normally open expiratory flow gradient delay cartridge 417. The line 573 is also connected by a line 574 to one side of the IMV on-off switch 182.

The termination of the inspiratory phase by volume limiting by operation of the inspiratory volume limiting switch 299 causes various functions to occur as hereinafter described, which includes the removal of gas under pressure in the line 534 so that the valve member 379 of the valve assembly 373 can return to its normally open position. As soon as this occurs, the gases within the canister 246 are permitted to pass out through the fitting 288 through the inspiratory transfer valve assembly 373 and into the large tube 371 and thence into the interior of the bellows 256. The cam shaft 249 and the master cam member 291 carried thereby are lowered so that the headed cam member 297 is no longer in engagement with the inspiratory termination switch 299 so that the line 384 is no longer dumped to the atmosphere. Downward movement of the master cam member 291 occurs until the master cam member 291 strikes the volume limiting stop member 301 which serves as a base line for the cam member. When the master cam member 291 strikes the volume limiting stop member 301, all of the gas which previously had been delivered into the canister 246 will have been transferred into the interior of the bellows 256. As hereinbefore explained, by adjustment of the compound knob or dial assembly 216, the base line provided by the volume limiting stop member 301 can be adjusted. The higher the member 301, the higher the base line and the less will be the volume which is contained in the bellows 256. Inversely, the lower the stop member 301, the greater the volume contained in the bellows 256. With the present arrangement it can be seen that the inspiratory gas during one inspiratory or inhalation phase is entrained within the canister 246 and then within the next expiratory or exhalation phase, the gas within the canister 246 is transferred to the interior of the bellows 256 so that it is ready for delivery during the next inspiratory or inhalation phase. In this way it can be seen there is no waste of gas and a precise volume of gas is delivered into the canister 246 and is then subsequently transferred into the interior of the bellows 256.

During the inspiratory phase gas is also supplied from the line 526 through a line 536 where it is metered through an inspiratory flow control valve assembly 194 which meters gas to the diaphragm side of an inspiratory flow accelerator cartridge 426. The cartridge 426 is a normally closed cartridge and thus the faster the flow through the control valve assembly 194, the sooner the cartridge 426 will move to the open position. The control valve assembly 194 is provided with a tapered valve so that the more it is opened, the faster will be the rate of flow. Thus, the slope representing the flow rate will be increasing. Gas will also be supplied to both sides of the check valve 537.

Because of the adjustable restricted orifice provided by the inspiratory flow acceleration control valve assembly 194, the pressure build-up in the chamber on the diaphragm side of the inspiratory flow accelerator cartridge 426 will take a period of time determined by the adjustment of the inspiratory flow acceleration control valve assembly 194. If the pressure build-up is insufficient to overcome the force of the spring provided in the inspiratory flow accelerator cartridge during the inhalation phase, the valve member will remain in a closed position and no additional inspiratory gas will be supplied from the line 501 through the line 578 to the secondary jets of the master venturi assembly 463 to augment the main or primary flow of gases into the canister 246 as hereinbefore described. When this is the case, the inspiratory flow rate is determined exclusively by the inspiratory flow rate control valve assembly 196. This will be the normal situation at very low rates of flow at pressure below a predetermined pressure as, for example, 18 psi below which the inspiratory flow accelerator cartridge 426 will not be activated. Since the average pressure used for intermittent positive pressure breathing therapy ranges from 12 to 16 psi, this permits approximately 180° rotation of the control knob of the inspiratory acceleration control valve assembly 194 on the right side of the knob for therapeutic purposes without activating the flow accelerator cartridge 426. The other 180° rotation of the knob of the inspiratory flow acceleration control valve assembly can be utilized for intensive care applications. For each rate of flow through the control valve assembly 194 which creates a pressure greater than a predetermined pressure as, for example, 18 psi or greater depending upon the adjustment of the spring in the flow accelerator cartridge 426, the rate at which the flow accelerator cartridge 426 opens will be dependent upon the slope established by the adjustable restricted orifice that meters gas from the line 501 to the line 578. This makes possible the rapid build-up of flow acceleration in the master venturi assembly 463 and the tubing connected thereto but prevents any initial square wave effect because there is always some retardation in the opening of the flow accelerator cartridge 426.

Whenever the inspiratory gas pressure supplied to the diaphragm side of the inspiratory flow accelerator cartridge 426 exceeds the spring pressure on the diaphragm provided therein, the tapered valve member will be moved to an open position against the force of the spring to permit source gas under pressure from the line 501 to pass into the line 578 and into the secondary jets of the master venturi assembly 463 to augment the flow of primary gases through the master venturi assembly 463.

As explained previously, the apneustic plateau cartridge is a normally closed cartridge and during the inspiratory phase is moved to the open position as soon as gas is supplied to its diaphragm from the sequencing servo 188 through the line 514 and the check valve 516. As soon as the valve member 518 of the cartridge 407 is moved to the closed position, source gas from the line 504 is supplied to a line 538 which supplies the source gas through the check valve 539 to load the diaphragm side of the normally open expiratory flow gradient delay cartridge 417. Another line 541 is connected to the line 538 and is connected through a check valve assembly 542 to load the diaphragm side of the normally closed PEEP termination cartridge 421. The source gas is also supplied to one side of the dynamic expiratory termination valve assembly 183. In addition, this source gas is supplied through a line 543 to one side of a one-way check valve assembly 544. Another line 546 connected to the line 541 is connected to a nebulizer orifice 547 and the other side of the orifice 547 is connected by line 548 to the inspiratory service socket of fitting 117. Normally, the fitting 117 is connected to the tube 128 which is connected to the jet of the small nebulizer 127. The small nebulizer is normally used for delivering medication such as bronchial dialator. However, in the event it is desired to deliver a tremendous amount of nebulization, then both jets of the 500 cc nebulizer 122 would be used, in which case the socket or fitting 117 would be connected to the tube 141. The nebulizer orifice 547 causes a controlled amount of gas to be delivered to the nebulizer jet. By way of example, it has been found that an orifice having a diameter of 0.024 inches under 50 psi will deliver 200 cc per second of gas to the nebulizer.

A line 551 is connected to the line 538 and is connected to one side of a check valve assembly 552. The other side of the check valve assembly 552 is connected by a line 553 to the expiratory time control valve assembly 187 which is connected by a line 554 to the diaphragm side of the normally open expiratory termination cartridge 418 to move the same to a closed position almost instantaneously when the respirator is turned on by the master on-off switch 204 and the respirator is cycled to the inspiratory phase by gas passing through the IMV assist-control selector swtich 181 to the sensing venturi assembly 461 to create a subambeint condition to cycle the sequencing servo 188 to the "on" position as hereinbefore described. The closing of the expiratory termination cartridge interrupts further flow of gas through the outer jets of the sensing venturi assembly 461. Gas is also supplied from the line 554 through a check valve 556 to the auxiliary reservoir 491. The auxiliary reservoir 491 is also connected to an adjustable orifice 557 which is also connected to the line 554. The purpose and operation of this auxiliary reservoir will be described hereinafter.

Gas is supplied from the line 551 through a line 558 through a check valve 559. The check valve 559 is connected by line 561 to an orifice 562. The orifice 562 is connected by a line 563 to the inlet side of a normally open lock-out cartridge 432. When the cartridge 432 is open, gas under pressure is supplied through a line 564 to the inspiratory service socket 116. This service socket 116 is connected to the tube 141 which is connected to the exhalation valve assembly 161 to move the same to a closed position and to retain the same in a closed position during the inspiratory phase. Gas can also be taken from the socket 116 and can be utilized for powering one of the jets in the 500 cc nebulizer 122 through the tee 139 provided on the exhalation valve assembly 161. Since an orifice of a controlled size as, for example, 0.024 of an inch has been provided in the form of the orifice 562, only a controlled amount of gas, i.e. 200 cc's at a 50 lb. source pressure, it supplied through the nebulizer jet into the breathing circuit. As pointed out previously, the inspiratory nebulization service socket 117 is only used when it is desired to deliver a medicine such as a bronchial dialator to the small nebulizer 127 into the patient circuit.

Gas is supplied from the line 563 through a line 566 through an orifice 567 and then through a line 568 to the diaphragm side of the lock-out cartridge 432. The orifice 567 is adjusted so as to pressurize the diaphragm of the lock-out cartridge 432 in a suitable time which is normally greater than the normal inspiratory time as, for example, 10 seconds. A reset check valve 569 is provided for dumping the gas on the diaphragm side of the lock-out cartridge during the expiratory phase. Thus, it can be seen that the lock-out cartridge when it moves to a closed position interrupts the flow of gas to the exhalation valve assembly 161 so that after a predetermined 10 seconds of time the exhalation valve assembly 161 is permitted to open.

As described in copending application Ser. No. 544,505, filed Jan. 27, 1975 now U.S. Pat. No. 3,974,828, when additional gas is desired in the patient breathing circuit, such gas will be supplied by the entrainment reservoir 483 through the check valve 473. If still further gases are required which are beyond the capabilities of the respirator, then atmospheric air can be introduced through the inlet filter 478 and through the check valves 472 and 473.

In the event that the respirator even with the entrainment reservoirs 483 is incapable of supplying sufficient flow rate to the patient during the inspiratory phase, additional flow requirements can be met by use of the gas stored in the accumulator chambers 386 and 387. This source of augmented or additional gas can be obtained during the inspiratory phase merely by operating the toggle switch 391. Gas under pressure is supplied from the line 534 at the commencement of the inspiratory phase to the diaphragm side of the normally closed accumulator discharge cartridge 389 to move the same to an open position to permit the gas which has accumulated within the accumulator chambers 386 and 387 to pass through the cartridge 389 and through the tube 393 and into the large tube 377 to increase the flow rate of gases to the patient through the fitting 113 in the upper cabinet, thence into the large tube 111 and finally to the patient as hereinbefore described.

In this connection, it has been assumed that the accumulator chambers 386 and 387 were filled with gases during the previous expiratory phase from the line 398. Whenever it is unnecessary to utilize the accumulator chambers 386 and 387, the toggle switch 391 is merely moved to a position so that the gas supplied to the line 534 will not be supplied to the cartridge 389. By the use of such accumulator means, it is possible to maintain elevated inspiratory flow when the desired delivery pressures exceed the entrainment gradient which can be obtained through the master venturi 463.

The flows of inspiratory gases hereinafter described during the inspiratory or inhalation phase of the respirator delivers inspiratory gases into the distal airways or ducts of the patient's lungs. Automatic nebulization occurs during the inspiratory phase because the inspiratory gases must pass through the 500 cc nebulizer 122 and the small nebulizer 127. The rate of inspiratory flow determines the rate of nebulization. As the flow rate is increased under the control of the flow rate control valve assembly 196, the pressure behind the primary jet of gases in the master venturi assembly 463 which increases the flow through the master venturi assembly 463 which carries with it gases from the entrainment reservoir 483 and if necessary, air from ambient through the inlet 478. These gases delivered by the master venturi assembly 463 in the inspiratory phase are delivered to the canister 246 as hereinbefore described. The inspiratory flow of gases into the canister includes flow of inspiratory gases parallel to the primary flow through the flow rate control valve 196, one of which is through the apneustic plateau flow rate control valve assembly 193, and the other of which is through the flow accelerator cartridge 426.

The flow of gases through the inspiratory flow accelerator cartridge 426, once it commences as hereinbefore described, continues throughout the inspiratory phase. Thus, there is provided a minimum flow of gases through the nebulizers 122 and 127 regardless of the slowing of the inspiratory flow rate near the end of the inspiratory phase. In this way it is possible to effectively increase the volume of particulate delivery from the nebulizers during slow flow techniques.

EXHALATION PHASE

Termination of the inspiratory phase occurs by volume limiting when the pressure in the line 384 is dropped to atmospheric through the inspiratory termination switch 299. When this occurs, the pressure on the diaphragm of the inspiratory termination cartridge 416 is relieved to permit the cartridge 416 to move to the normally open position. This permits the gas to flow from the line 507 through the inspiratory termination cartridge 416 into line 570 to the diaphragm side of the inspiratory termination valve assembly 467 to move the same to a closed position to prevent further inspiratory gases to be delivered to the tube 377. The closing of the inspiratory termination valve assembly 467 causes an almost immediate increase in pressure in the sensing venturi assembly 461. The pressure in the sensing venturi 461 is sensed through the line 581 which is in communication with the diaphragm side of the sequencing servo cartridge 188. This increased pressure causes the diaphragm 511 and the plunger 512 carried thereby to be moved upwardly as viewd in FIG. 13 so that the source gas in the line 502 can no longer be supplied to the line 514. Bleed down of the gas under pressure behind the diaphragm occurs through the orifice 575 through the flapper valve 473 to the master venturi assembly 463 of the valve assembly 467.

Upon termination of the inspiratory phase by volume limiting, there still will be apneustic flow from the source gases through line 504 through the apneustic plateau cartridge through line 538, line 546, orifice 547, line 548 and through the inspiratory nebulization servo socket 117 to provide nebulization gases either for the small nebulizer 127 or the large nebulizer 122. This apneustic flow continues for a period in the manner hereinafter described.

If it is desired to utilize pressure limiting rather than volume limiting, it is merely necessary to operate the switch 212 so that the diaphragm side of the inspiratory transfer valve assembly 373 is not exposed to the line 534. This insures that the inspiratory transfer valve assembly 373 will remain in an open position so that gas can readily pass through the tube 377 directly to the tube 378. When this is the case, the inspiratory phase will be pressure or time limited. The sensing venturi 461 supplies the pressure information to the sequencing servo 188. In addition, the airway pressure is monitored by the auto-sensitivity cartridge 422. The increased pressure transferred from the sensing venturi assembly 461 to the sequencing servo 188 causes the diaphragm 511 to move upwardly and to carry therewith the operating rod or plunger 512 which moves the valve member 513 into a seating engagement with the valve seat to prevent further flow from the source passage 502 into the passage 514.

The supply of source gas through the line 514 to the diaphragm side of the apneustic plateau cartridge 407 is also interrupted. As soon as this occurs, the diaphragm side of the apneustic plateau cartridge 407 will be bled down through the apenustic plateau control valve assembly 193 and then through the line 581 and into the entrainment reservoir 483. During the time that the diaphragm side of the apneustic plateau cartridge 407 is being bled down, source gas is continued to be supplied under pressure through the line 538 and then through the line 546 and line 548 to the inspiratory nebulization service socket 117 so that there is provided a topping low flow which is introduced into the patient's breathing circuit during the period of apneustic hold which is encountered after the termination of the inspiratory phase. This topping low flow continues until the apneustic plateau cartridge 407 has been bled down sufficiently to permit the valve member 518 to move to a closed position to terminate the flow of source gas from the line 504 to the line 541.

At the same time that apneustic flow is terminated through the line 538 the apneustic flow is also terminated through the line 551 so that pressure no longer is applied to the exhalation valve 161 and permits the same to open and to thereby permit commencement ot the expiratory phase by permitting the patient to exhale through the exhalation valve assembly 161.

At the time that the sequencing servo 188 is sequenced from the inspiratory phase to the expiratory phase, gas on the diaphragm side of the expiratory flow cartridge 406 is bled out through the flow rate control valve 196, the line 526, the check valve 527 and into the master venturi assembly 463. As soon as this occurs, which is relatively rapidly because of the high flow rate, source gas under presure is supplied from the master on-off switch through the line 502, the line 506, the line 507 through the expiratory flow cartridge 406 and thence into line 571, the line 572, the line 573 to the inlet side of the expiratory flow gradient delay cartridge 417. This gas in the line 573 is also supplied to a line 574 which is connected to one side of the IMV on-off switch 182. Gas is also supplied to the line 576 to the inlet of the reservoir demand flow accelerator cartridge 428. If the entrainment reservoir 483 was emptied or partially emptied during the previous expiratory phase, the reservoir demand flow accelerator cartridge is operated to permit the gas the flow directly into the entrainment reservoir. This will continue during the expiratory phase until the desired pressure has been reached in the entrainment reservoir at which time this pressure will be sensed by the reservoir demand flow accelerator cartridge 428 and will terminate further flow from the line 576 into the entrainment reservoir. Gas is also supplied from the line 576 to the line 398 which is connected to the inspiratory flow boost accumulator. Gas is also supplied from the line 571 through a check valve 586 to the inspiratory time control valve assembly 189 which is connected by a line 587 to the diaphragm side of the inspiratory termination cartridge 416. The line 587 is connected to the line 384 which is connected to the inspiratory volume limiting switch 299.

At the time of termination of flow of source gases through the line 538 from the apneustic plateau cartridge 407, the peep termiation cartridge 421 and the expiratory flow gradient delay cartridge 417 are bled down. The peep termination cartridge 421 is bled down through the adjustable dynamic expiratory termination valve 183 and thence through a line 582 to the line 581 and thence into the entrainment reservoir 483. The diaphragm side of the expiratory flow gradient delay cartridge 417 is bled down through the expiratory flow gradient delay control valve assembly 192 and also into the lines 582 and 581 into the master venturi assembly 461. By adjusting the valve assemblies 183 and 192, it can be seen that the rate at which the cartridges 421 and 417 are moved to other conditions can be controlled. Thus, the adjustment of the valve assembly 183 determines when the peep termination cartridge wll be moved to its normally closed position and similarly the expiratory flow gradient delay control valve similarly the expiratory flow gradient delay control valve assembly 192 can be utilized for determining when the expiratory flow gradient delay cartridge 417 will be returned to its normally open position.

As hereinbefore explained, the expiratory flow gradient delay cartridge 417 delays the application of the constant positive airway pressure (CPAP) until near the end of the exhalation phase to allow unrestricted exhalation by the patient.

Thus, after a predetermined period of time, the diaphragm side of the expirator flow gradient delay cartridge 417 is bled down permitting the cartridge to move to is normally open position and permitting expiratory gases to flow from the line 573 through the cartridge 417 and into the line 632. Assuming that the timing for the bleed down on the Peep termination cartridge 421 is greater than that for the cartridge 417, the Peep termination cartridge 421 will be in an open position permitting inspiratory gases to flow through the same into the line 641 and through a check valve 642 into a line 643 and thence through the expiratory flow gradient control valve assembly 191 through the line 593 and through the socket 114 to tube 176 and from there through the jet of the tee 171 to cause application of pressure to the exhalation valve assembly 161 so that the patient thereafter must exhale against a positive pressure. After a certain predetermined time as determined by the bleed down rate from the Peep termination cartridge 421, the positive end expiratory pressure applied by the Peep termination cartridge 421 is terminated by the cartridge moving to its normally closed position and preventing the flow of any further gas from the line 632 to the inlet of the Peep termination cartridge 421. Thus, it can be seen that the expiratory flow gradient delay cartridge 417 determines when the positive end expiratory pressure will be applied in the expiratory phase and the Peep termination cartridge 421 determines when this positive airway pressure will be terminated.

The inspiratory flow accelerator cartridge 426 moves to its normally closed position immediately after operation of the sequencing servo 188. This occurs because as soon as source gas from the line 502 is interrupted by the ball valve 513 no further gas is supplied to the line 514. This occurs because the diaphragm side of the inspiratory flow accelerator cartridge is dumped immediately to the atmosphere through the check valve 537 through the line 536 and then through the check valve 527 into the master venturi assembly 461. This terminates all flow through the inspiratory flow accelerator cartridge 426 from the line 501 and into the line 528.

At the time the apneustic plateau cartridge 407 moves to its normally closed position the gas is no longer supplied to the inspiratory nebulization service socket and therefore the exhalation valve assembly 161 will be permitted to move to an open position to permit the patient to exhale to the atmosphere.

As soon as the patient has a completed exhalation and attempts to inhale, a sub-ambient condition will be created in the breathing circuit to the patient which will be sensed by the sensing venturi 461. This sub-ambient condition will be transmitted through the line 581 to the sequencing servo 188 which will cause the diaphragm 511 to be pulled downwardly to open the ball valve 513 to terminate the inhalation phase phase by pressure to again permit source gas to flow through the sequencing servo 188 and into the line 514 to cause commencement of the inspiratory phase and the subsequent operations of the type hereinbefore described.

The expiratory rate for the exhalation phase can also be terminated by time under the control of the expiratory time conrol valve assembly 187. At the commencement of the expiratory or exhalation phase, gas will be bled out from the diaphragm side of the expiratory termination cartridge 418 through the expiratory time control valve assembly 187 into the line 581 into the entrainment reservoir. During this bleed off, there will also be some gas bled out from the auxiliary reservoir 491 through the bleed orifice 557. When the expiratory time control valve assembly is set for relatively high rates of flow and relatively short expiratory times, there will be relatively little flow from the auxiliary reservoir 491. However, when the expiratory time control valve assembly 187 is set for relatively long flow times, there will be significantly more gas bled from the auxiliary reservoir 491 through the feed orifice 557. The use of the auxiliary reservoir is advantageous in that it makes it possible to utilize a relatively coarse expiratory time control valve assembly while still obtaining relatively precise expiratory times because the flow rate is maintained at a relatively high value by the bleed off from the auxiliary reservoir 491.

When the expiratory termination cartridge 418 returns to its normally open position, source gas will be supplied from th line 503 through the expiratory termination cartridge 418 through the line 508 and depending upon the position of the IMV assist-control selectors, gas will either be supplied through the check valve 509 and the line 510 to the outer jets of the sensing venturi or alternatively will be supplied to the check valve 616 through the manifold 617 through the IMV assist cartridge 429, the line 619 to the center jet of the sensing venturi assembly 461. In either event, a subambient condition will be created within the sensing venturi to cause the sequencing servo 188 to move downwardly to open the valve to permit flow from the source to the line 522 to thereby initiate the inspiratory phase and the sequence of operations hereinbefore described.

Let it be assumed that during operation of the respirator it is desired to utilize intermittent mandatory ventilation. This is accomplished by moving the IMV on-off switch 182 to the on position. When this occurs, the expiratory flow from the line 574 is supplied to a line 591. The gas from the line 591 passes through a check valve 592 through the expiratory flow gradient control valve assembly 191 through a line 593 to the expiratory flow gradient service socket 114 to the tube 176 and the jet on tee 171 to cause a constant positive pressure to be applied against which the patient must exhale. The gas is also supplied from the line 591 through a line 594 through a check valve 596 and then through a restricted orifice 597 through a line 598 to the expiratory nebulization service socket 118 which provides gas to the tube to the 500 cc nebulizer 122 for humidification of gases which the patient may inhale. Gas is also supplied from the line 591 through a line 601 through the check valve 544, the line 543 to the diaphragm side of the normally open expiratory flow gradient delay cartridge 417 to move the same to a closed position to thereby lock out the expiratory flow gradient cartridge 417 during the time that IMV procedures are being utilized.

Gas is also supplied from the line 591 to a line 602 which is connected to the inlet side of the IMV demand flow accelerator 423. A line 603 is connected to the line 602 and is connected to a demand flow damper 604. During operation of the IMV circuit, the IMV demand flow accelerator 423 furnishes gas to the patient breathing circuit when the patient breathes spontaneously during the IMV phase. When the patient takes a breath the pressure drop is sensed by the airway pressure monitor 186 in the line 606 which is connected to the airway presure monitoring socket 119. A line 606 is connected to the diaphragm side of the IMV demand flow accelerator 423 and thus senses when a low pressure is reached to permit the normally closed IMV demand flow accelerator to move an open position to permit gas flow to the patient. This is accomplished by gas flowing from the line 502 through the line 506, the line 507 and thence through the expiratory flow cartridge 406 through the line 571, the line 572, the line 573, the line 574 through the IMV on-off switch 182 through the line 591, the line 602 to the IMV demand flow accelerator 423 through line 608, through the isolation check valve 609 and thence into the line 528 into the master venturi assembly 463. Gas is also supplied from the line 608 through a line 611 to the diaphragm side of the IMV assist cartridge 429. Gas is also supplied to a line 612 through a check valve 613 which is connected to the line 566. This gas passes through the lock-out cartridge 432 and into line 564 to the inspiratory service socket where the gas is used for closing the exhalation valve assembly 161 and for powering nebulizers as hereinbefore described. The line 566 is connected to the lock-out time control cartridge 567 and the line 563. To prevent chattering of the IMV demand flow accelerator 423 at low flows, the demand flow damper 604 has been provided which supplies gas a controlled rate through a line 614 to the line 606 to flood the sensing line 606 in the diaphragm side of the demand flow accelerator 423 to prevent it from chattering. The check valve 527 serves as an isolation check valve to prevent IMV flow into the line 526 which could pressurize the inspiratory line and activate the apneustic plateau cartridge 407 and cause other malfunctions.

It can be seen from the foregoing that the lockout cartridge 432 will lock out apneustic flow, all flow coming out of the sequencing servo 188 and also all IMV flow from the line 566, after a predetermined lock out time as, for example, 10 seconds, so that in effect any flow entering the inspiratory service socket 116 from all three of these primary sources in he event that the respirator for some reason is stuck in the inspiratory phase would be interrupted after 10 seconds because of operation of the lock-out cartridge 432.

It also can be seen from the foregoing that when the patient takes a breath and causes operation of the IMV demand flow accelerator cartridge 423 to an open position, gas will be supplied through the line 611 to the diaphragm side of the normally closed IMV assist cartridge 429 to move the same to open position. Assuming that the IMV assist-control selector switch 181 is in the position shown, gas under pressure is supplied from the line 502, from the master on-off switch 204 through the normally open expiratory termination cartridge 418 through the IMV assist controlselector switch 181 through a check valve 616 through a manifold 617 through a line 618 to the IMV assist cartridge 429 through a line 619 to the central jet of the sensing venturi assembly 461. Thus, it can be seen that when the IMV assist-control selector switch 181 is in the operative position, gas will be delivered to the sensing venturi assembly 461 each time the IMV assist cartridge 429 is moved on to an open position in response to each time the patient takes a breath as hereinbefore described. With the arrangement shown, the IMV assist cartridge 429 is loaded with gas and is ready to deliver the gas as soon as it is operated by the patient taking a breath.

Now, let it be assumed that the patient for some reason has not taken a breath. When this is the case, the IMV assist cartridge 429 will be loaded with gas through the expiratory termination 418 in the manner hereinbefore described. At the same time gas is supplied from the manifold 617 through a line 621 to an assist-control delay meterin valve 622 and then through a line 623 to the diaphragm side of a normally closed IMV control cartridge 427. Within a predetermined period of time as, for example, a period ranging from four to five seconds as determined by the metering valve 622. the IMV control cartridge 427 will be moved to an open position to permit gas from the manifold 617 to pass therefrom through a line 624 through the IMV control cartridge 427 through a line 626 to the line 510 and to the secondary jets of the sensing venturi assembly 461. As soon as the respirator is shifted into the inspiratory phase, the expiratory termination cartridge 418 is shifted to a closed position which interrupts flow into the manifold 617. This permits the gas in the diaphragm side of the IMV control cartridge 427 to be bled down through the reset check valve 628 into the manifold 617. The manifold 617 is bled down to the atmosphere through the line 624, the IMV control cartridge 427 and the sensing venturi assembly 461.

The manifold is also connected to a line 629 which is connected through a check valve 631 to a line 632 which is connected to the inlet side of a normally closed autosensitivity cartridge 422. The diaphragm side of the autosensitivity cartridge is connected by a line 636 which is connected to a line 606 which, as described previously, is connected to the airway pressure monitoring socket 119. The signal which is received at the airway pressure monitoring socket 119 is supplied to the auto-sensitivity cartridge 422 which has a large diaphragm and is very sensitive to any reduction in the airway pressure such as by the patient taking a small breath. This change in pressure is sensed by the auto-sensitivity cartridge 422 and causes the same to open the normally closed valve and expiratory flow gases from the line 632 are supplied through the cartridge 422 to a check valve 637 which delivers gas through a line 638 which is connected to line 510 and thus delivers gas to the secondary jets of the sensing venturi assembly 461. As hereinbefore explained, expiratory flow during the expiratory phase comes from the expiratory flow cartridge 406 through line 571, line 572, line 573 to the normally open expiratory flow delay cartridge 417 and thence into the line 632 which as hereinbefore explained is connected to the inlet of the auto-sensitivity cartridge 422. Thus, it can be seen that when the patient takes a breath, the auto-sensitivity cartridge 422 will be triggered which is another means of insuring that the inspiratory phase will commence when it should.

RESPIRATOR WITHOUT VOLUME LIMITING

In the event that it is desired to provide a respirator which does not have the volume limiting features hereinbefore described, the lower cabinet 32 can be removed and all of the tubes extending from the lower cabinet into the upper cabinet can be eliminated. It is only necessary to provide internally of the upper cabinet 31 a large tube (not shown) represented by the arrows 651 in FIG. 13 which connects the part which is normally connected to the tube 377 to the part which is normally connected to the tube 378 so that there is a connection established between the breathing circuit to the patient and the master venturi assembly 463. In addition, the lines 534, 384 and 398 are capped. Thus, it can be seen that it is a relatively simple matter to separate the top cabinet and to form a separate module from the same and thereby only losing the volume limiting feature provided by the lower cabinet 32. The upper module still would have pressure and time limiting capabilities of the type hereinbefore described.

ANESTHESIA UNIT

Figure 14:
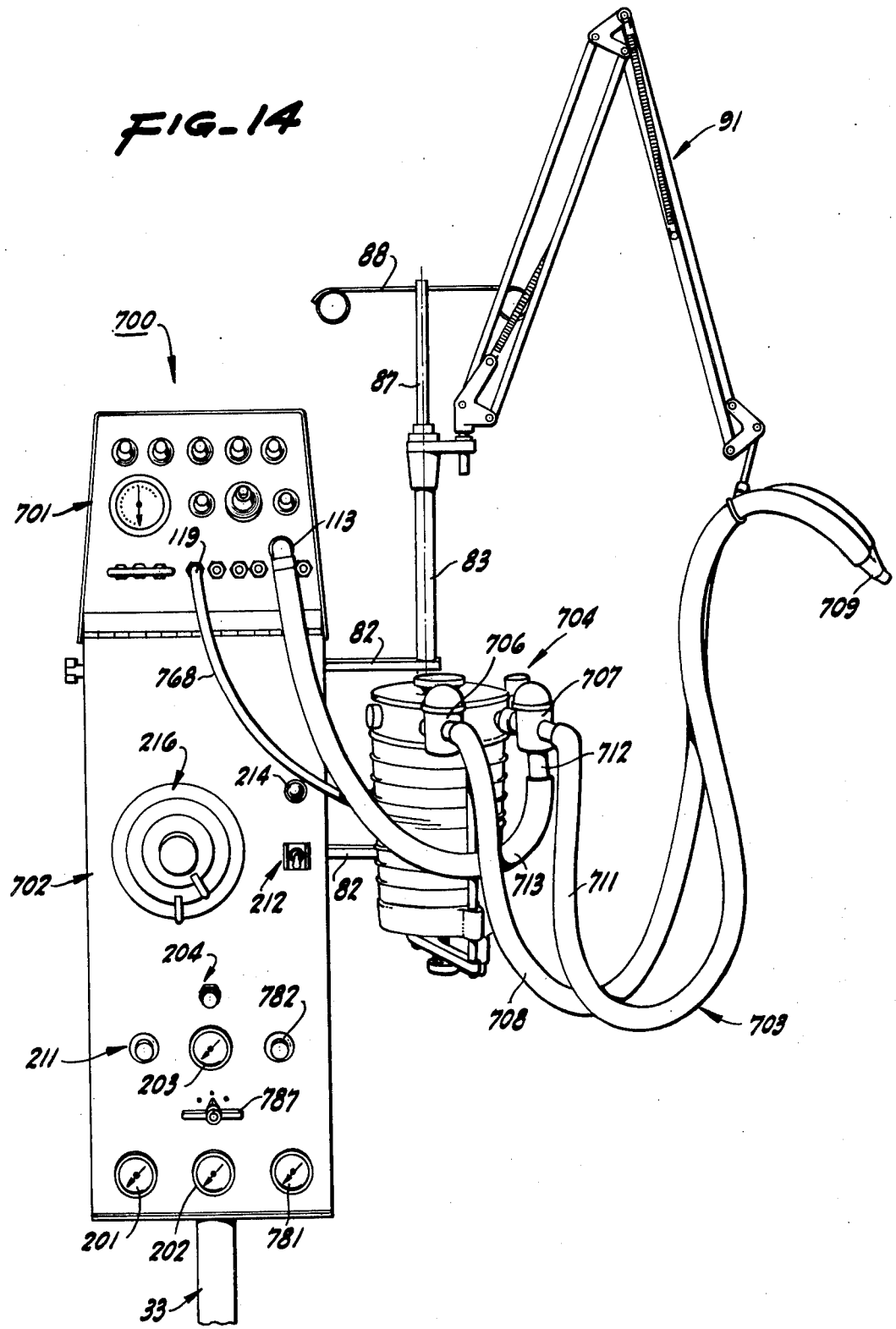
FIG. 14 is a front elevational view of a respirator incorporating the present invention which can be utilized for administering anesthesia.
Figure 15:
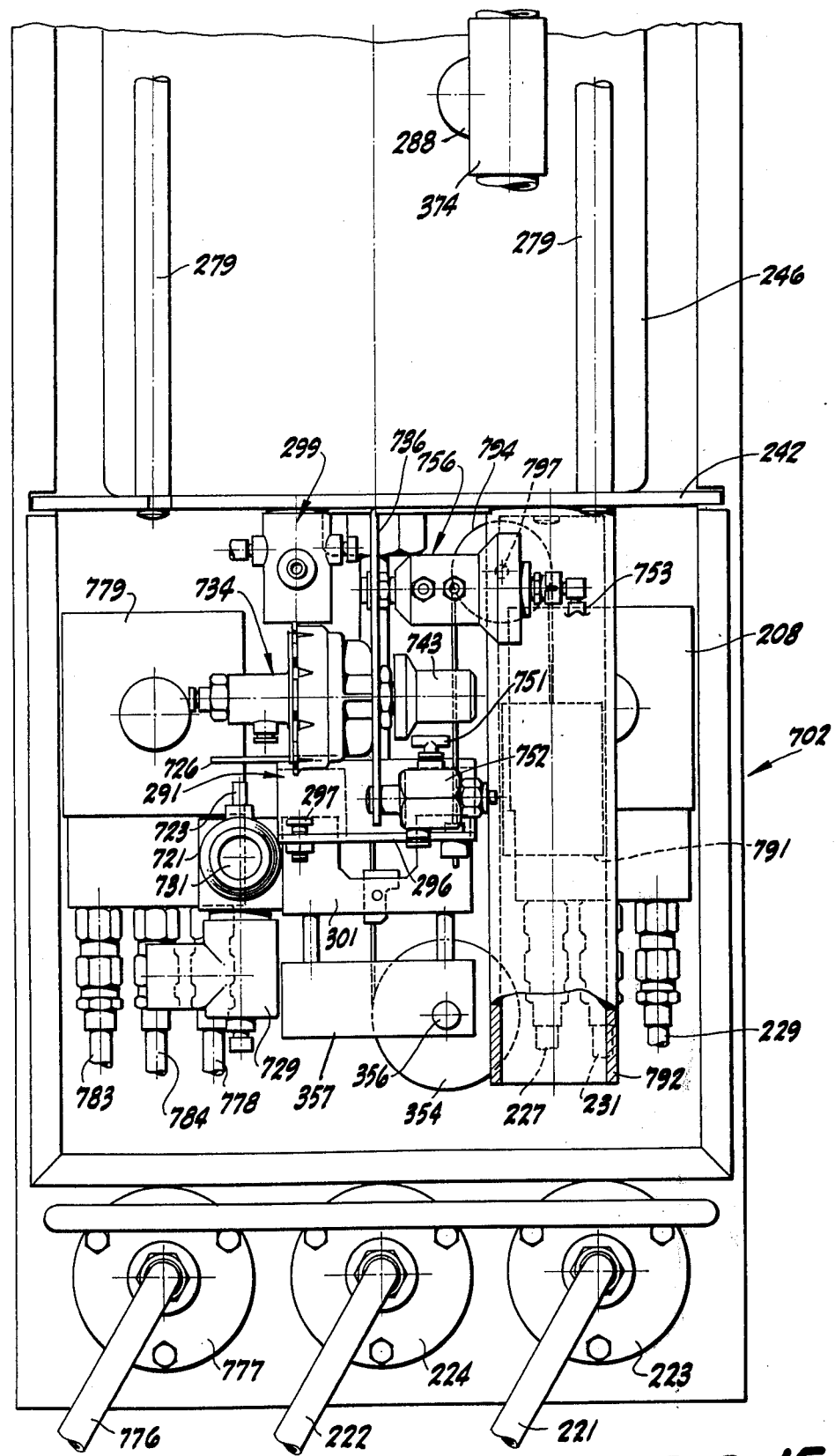
FIG. 15 is a rear elevational view of the portion of the respirator shown in FIG. 14.
Figure 16:
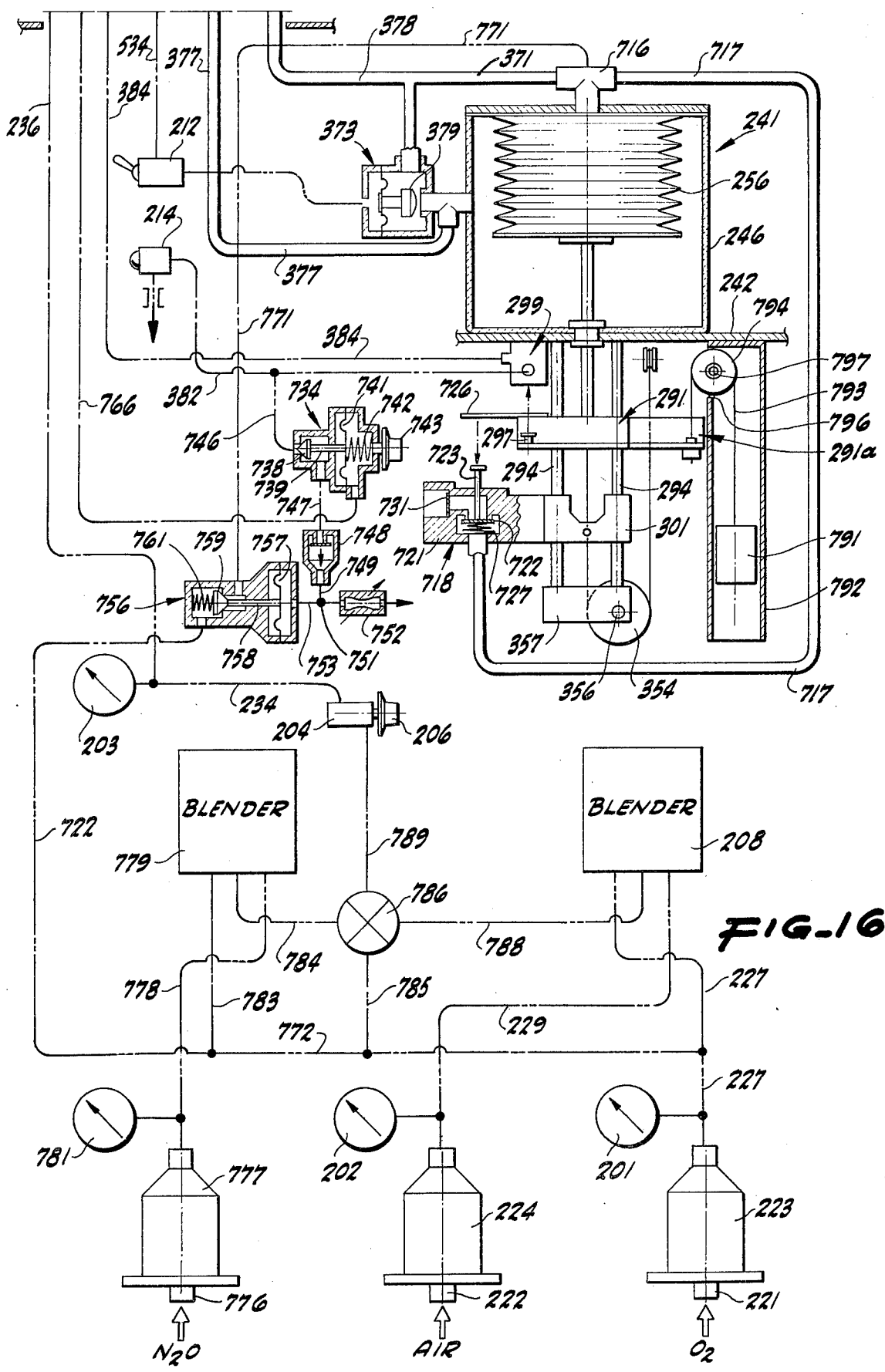
FIG. 16 is a flow diagram which is partially in schematic form, showing the mode of operation of the respirator shown in FIGS. 14 and 15 used as an anesthesia unit.

An anesthesia unit 700 is shown in FIGS. 14, 15 and 16 and as can be seen therefrom, it is very similar to the respirator or ventilator 30 which has been described in conjunction with FIGS. 1-13. As shown in FIG. 14, it includes an upper cabinet 701 which can be identical to the upper cabinet 31 provided in the respirator 30. It also includes a lower cabinent 702 which is similar to the lower cabinet 32 except for certain additions hereinafter hereinafter described. The lower cabinet 702 is mounted on the castered stand 33 of the type hereinbefore described. The breathing circle system utilized in conjunction with the respirator shown in FIGS. 1-13 has been removed and an anesthesia circle system 703 has been mounted upon the lower cabinet 702. The anesthesia circle system is of a conventional type and includes a carbon dioxide ($CO_2$) absorber 704, such as one manufactured by Ohio Medical Products of Madison, Wisconsin, and also of the type disclosed in U.S. Pat. No. 3,088,810. The $CO_2$ absorber 704 has mounted thereon an inspiratory one-way valve assembly 706 and an expiratory one-way valve assembly 707. The inspiratory one-way valve assembly is connected to a large tube 708 which is connected to a wye 709. Another large tube 711 is connected to the expiratory one-way valve assembly 707 and is also connected to the wye 709. The wye 709 is adapted to be connected to a patient adapter to be carried by the support arm assembly 91 as shown. Conventionally, the expiratory one-way valve assembly 707 is provided with the fitting 712 and has mounted thereon a flexible reservoir bag which fills with gas containing the anesthesia agent which is inhaled and exhaled by the patient. However, in the present anesthesia unit, this bag is removed and a large tube 713 is connected thereto and is connected to the breathing tube receptacle 113 provided in the upper cabinet 701 and which is internally connected to the bellows inside of the lower cabinet 702 as hereinafter described and which acts as a reservoir bag for anesthesia gas.

As can be seen from FIG. 16, the large tube 378 is connected to the inspiratory transfer valve assembly 378 is connected to the inspiratory transfer valve assembly 373, as in the respirator shown in FIGS. 1-13 and the large tube 371 is connected to the tube 378. It is connected into a tee 716 provided at the top of the canister 246. As can be seen, the tee 716 is in communication with the interior of the bellows 256. The tee 716 is connected by a large tube 717 to a gas balance valve assembly 718. The gas balance valve assembly 718 is secured to the volume limiting stop member 301 by suitable means such s a bracket (not shown) and screws (not shown). The gas balance valve assembly consists of a body 721 which is secured to the braket hereinbefore described.

A conical poppet valve 722 is provided within the body and is carried by a valve stem 723, which extends out of the body. The valve stem 723 is adapted to be engaged by an arm 726 which is mounted upon the master cam member 291 to move the member 722 to an open position against the force of a spring 727 provided within the body 721. A 90° elbow 729 is mounted on the body 721 and has the tube 717 connected thereto. A check valve in the form of a flapper valve 731 is mounted in the body 721 and prevents atmospheric air from entering into the body 721 and permits the gas to flow from the line 717 past the valve member 722 when it is in the open position and past the flapper valve 731 to the atmosphere for a purpose hereinafter described.

Additional parts and components are mounted in the lower cabinent 702 and as shown in FIG. 15 includes a demand flow accelerator cartridge 734 which is mounted upon an L-shaped bracket 736 secured to the bottom side of the plate 242. The demand flow accelerator cartridge 734 includes a valve member 738 which is carried by a valve stem 739 (see FIG. 16) which is connected to a diaphragm 741. Means is provided for adjusting the pressure applied to the diaphragm and to the valve member 738 and includes a spring 742 engaging the diaphragm and an adjustment knob 743 for adjusting the force applied by the spring 742 to the diaphragm 741. The inlet to the demand flow accelerator cartridge 734 is connected by a line 746 to the line 382 which is connected to the inspiratory termination switch 299. The outlet of the demand flow accelerator cartridge 734 is connected by a line 747 to a one-way check valve assembly 748. The other side of the check valve assembly 748 is connected by a line 749 to a tee 751 which is mounted on an adjustable refill timing valve assembly 752, which is mounted upon the bracket 736. The valve assembly 752 has one end open to the atmosphere as shown in FIG. 16. The tee 751 is connected to the line or tube 753 which is connected to the diaphragm side of a normally closed flow valve assembly 756 which is alo mounted upon the bracket 736. The valve assembly 756 is provided with a diaphragm 757 which engages a valve stem 758 that carries a valve member 759. The valve member 759 is normally yieldably urged towards a closed position by a spring 761.

The diaphragm side of the demand flow accelerator cartridge 734 is connected by a line 766 to the airway pressure monitoring socket 119 provided in the top or upper cabinet 701 in a suitable manner such as by connecting the same into the line 606 as shown in FIG. 13. As shown in FIG. 14, the airway pressure monitoring socket 119 has a tube 768 connected and which is connected to the expiratory one way valve assembly 707 to monitor the pressure of the gases in the breathing circuit of the patient.

The outlet of the flow valve assembly 756 is connected by a tube 771 to the tee 716. The tee 716 is provided with an orifice which controls the rate of flow from the line 771 to a suitable value, for example, a flow of approximately 30 liters per minute. The inlet of the valve assembly 756 is connected by a tube 722 to the oxygen line 227.

In addition to the source of oxygen and air provided in the respirator shown in FIGS. 1-13, there is provided means for supplying suitable anesthesia gas to the anesthesia unit 700 which includes an additional line 776 (see FIG. 15) which is connected to a suitable source (not shown) of anesthesic gas.

By way of example, this anesthesia agent can be nitrous oxide ($N_2O$) which is supplied in gaseous form to the tube 776 and through a filter 777 mounted in the lower cabinet 702. The gas from the filter 777 is supplied through a line 778 to a blender 779. The blender 779 is of the same tupe as the blender 208. The pressure of the anesthesic gas supplied through the line 778 is monitored by the pressure meter 781. The blender 779 is provided with a control knob 782 accessible from the front side of the cabinet for adjusting operation of the blender. A line 783 is provided for connecting the oxygen line 772 to the blender 779. The output of the blender 779 is connected by a line 784 to a conventional three-way valve assembly 786 which is mounted on the lower cabinet 702 and is provided with a control handle 787 accessible on the front side of the cabinet. A line 785 connects the three-way valve assembly 786 to the oxygen line 772. Another line 788 connects the output of the blender 208 to the three-way valve assembly 786. The output from the three-way valve assembly 786 is connected by a line 789 to the master on-off switch 204, which serves its conventional function. If desired, a conventional pressure regulator (not shown) can be provided in the line 789 so that gas under a predetermined pressure is supplied to the master on-off switch 204.

In order that the bellows system provided in the anesthesia unit 700 will not inhibit spontaneous breathing by the patient utilizing the anesthesia unit, counterweight means is provided for counterweighting the mass of the bellows system 241. This counterweight means can take any suitable form and as shown in FIGS. 15 and 16, it takes the form of a cylindrical weight 791 which is free to move vertically in a cylindrical tube 792 formed of a suitable material such as plastic which is open at its bottom end and is secured to the plate 242. The weight is carried by a small flexible cable 793 which extends upwardly in the tube 792 and travels over a pulley 794 and then travels downwardly where it is secured to an extension member 291a provided on the master cam member 291. The pulley 794 is mounted in a slot 796 provided in the upper end of the tubular member 792 and is rotatably mounted upon a pin 797 mounted in the sidewall of the tubular member 792.

OPERATION OF ANESTHESIA UNIT

Operation of the anesthesia unit may now be briefly described as follows. The controls provided in the upper cabinet 701 can be adjusted in the manner hereinbefore described in conjunction with the respirator. In the lower cabinet 702 the toggle switch 212 is placed in the upper volume limiting position shown in FIG. 16. The compound knob assembly 216 is adjusted to provide the proper bellows volume for the patient and by shifting the volume limiting stop member 301 serves as the base line for the bellows. The control knobs 211 and 782 on the blenders 208 and 779 are adjusted so that the desired ratio of gases is supplied to the master on-off switch 204.

Let it be assumed that the master on-off switch 204 has been turned to the "on" position. Let it also be assumed that the anesthesia unit has just completed an exhalation phase and that it is desired to commence an inspiratory or an inhalation phase. As explained previously in conjunction with the operation of the respirator, the sensing venturi 461 detects a subambient condition which is supplied to the sequencing servo 188 and as hereinbefore explained, supplies gas to the line 534 through the switch 212 to pressurize the diaphragm side of the inspiratory transfer valve assembly 373 to move the valve member 379 to a closed position. At this same time, main stream air flow is introduced into the large tube 377 from the top or upper cabinet 701 in the same manner as described in conjunction with the respirator, with the only change being that the gases which are introduced into the tube 377 contain an anesthesia gas. These gases are supplied to the canister 246 because the valve member 379 is in a closed position.

As the inspiratory anesthesia gases are delivered to the canister 246, the bellows 256 is caused to be raised in the manner hereinbefore described to cause the gases contained in the bellows to be forced through the tee 716 into the line 371 and into the line 378 where they are supplied to the breathing tube receptacle 113 and then into the tube 711 to the wye 709 and into the patient adapter (not shown) and into the lungs of the patient. This delivery of anesthesia gases from the bellows 256 continues until termination of the inspiratory phase which can be terminated either by pressure limiting, time limiting or by volume limiting in the manner hereinbefore described in conjunction with the operation of the respirator in FIGS. 1–13.

If pressure limiting occurs first, this condition will be sensed in the same way it is sensed in the respirator and the sequencint servo 188 will be switched to terminate flow from the line 502 into the line 514. The inspiratory phase can be terminated at any time by the bleed off of gases from the diaphragm side of the inspiratory termination cartridge 416 through the line 646 which is connected into the line 581, and which is in communication with the master venturi assembly 463 through the flapper valve 473. Thus it is possible that the anesthesia unit can go to the inspiratory phase either by pressure cycling or time cycling without the master cam member 291 coming into contact with the inspiratory termination switch 299. As soon as the inspiratory phase is terminated and the exhalation phase commences, the gas supplied to the line 534 is interrupted and thus the valve member 379 is permitted to return to an open position. This permits the gas within the canister 246 to be delivered through the inspiratory transfer valve assembly 373 and through the tee 716 into the interior of the bellows 256. At the same time the exhaled gases from the patient are delivered to the wye 709 through the large tube 708 and into the $CO_2$ scrubber 704 after which they are delivered to the tube 713 and returned to the fitting 113 provided in the upper cabinet 701. Thereafter, these exhalation gases are returned through the tube 377 and through the transfer valve 373 and into the tube 371 into the tee 716 and into the interior of the bellows 256. These gases which are introduced into the interior of the bellows 256 cause the bellows 256 to move downwardly and to raise the counterweight 791. This movement continues until the exhalation phase is terminated and the inspiratory phase is commenced. The exhalation phase can be terminated by the patient taking a breath and creating a subambient condition in the sensing venturi 461 to cause operation of the sequencing servo 188 in the manner hereinbefore described. The same sequence of operations will again occur in which the canister 246 is filled with gas, forcing the gas within the bellows 256 to the lungs of the patient.

From the foregoing it can be seen that the anesthesia unit works as a closed type system. However, it should be appreciated that at all times that there is additional gas flow into the system to maintain adequate oxygen concentrations in the gases and also to bring fresh anesthesia gas into the breathing circuit.

If the gas inflow into the circuits into the anesthesia unit is sufficiently high, the bellows 256 will reach the bottom of its stroke to recycle as determined by the positioning of the volume limiting stop member 301 as controlled by the compound knob assembly 216. The combination of the patient's exhaled gases delivered through te line 378 and the new gases within the canister 246 supply the total inflow to the bellows 256. If there is any excess gas, the excess gas will be discharged through the gas balance valve assembly 718. This occurs when the master cam member 291 bottoms out on the base line formed by the volume limiting stop member 301 and by the arm 726 striking the valve stem 723 to move the poppet valve 722 to an open position to permit the excess gas to travel through the line 717 and be dumped through the gas balance valve through the check valve 731 and to be dumped to the atmosphere or alternatively to be dumped into a suction system which may form part of a hospital used for collecting excess of discharged anesthesic gases.

Upon the upstroke of the master cam member 291 if there is insufficient gas in the bellows 256 to complete the inspiratory phase, the headed cam member 297 will strike the plunger (not shown) provided in the switch 299. When this occurs, gas will be supplied from the line 384 through the switch 299 through the line 382 and through the line 746 into the inlet of the demand flow accelerator cartridge 734. This demand for additional anesthesia gases will be sensed through the line 766 by the diaphragm side of the demand flow accelerator cartridge to move the valve member 738 to an open position to permit gas under pressure to be introduced through the check valve 748 into the diaphragm side of the normally closed flow valve assembly 756 to move the valve member 759 to an open position to permit 100% oxygen to be passed from the line 772 to the line 771 which is connected into the tee 716 to deliver the oxygen at a controlled rate as, for example, a rate of 30 liters per minute to fill the bellows. This filling continues until the diaphragm side of the normally closed flow valve assembly 756 has been bled down sufficiently through the adjustable timing valve assembly 752 to permit it to move to its normally closed position.

From the foregoing it can be seen when the bellows rises sufficiently to cause operation of the switch 299, flow is delivered to the inlet of the demand flow accelerator cartridge 734. The diaphragm side of the demand flow accelerator cartridge 734 is always "looking a pressures" within the bellows 256. When the peak inspiratory pressures in the bellows 256 are below a predetermined value as, for example, below 15 cm of water or the present opening pressure of the demand flow accelerator cartridge 734, the demand flow accelerator cartridge 734 is moved to an open position passing flow into the pneumatic delay circuit which includes the check valve assembly 748, the normally closed valve assembly 756 and the timing valve assembly 752. When the diaphragm side of the normally closed valve 756 is pressurized or loaded, oxygen is supplied to the bellows 256 in the manner hereinbefore described. The direction of flow is determined by the preset bleed down provided by the timing valve 752. Thus, it can be seen that the bellows 256 can be filled during a volume limiting procedure. This is made possible because the demand flow accelerator cartridge 734 serves as a pressure sensing device. If a reasonable peak delivery pressure of inspiratory gas has not been reached when the inspiratory termination switch 299 is activated the demand flow accelerator cartridge 234 is already open and activates the refilling circuitry hereinbefore described.

As hereinbefore explained, the bellows system 241 is balanced by the counterweight system which includes the counterweight 791. This permits spontaneous respiration by the patient through the anesthesia breathing circle using the bellows as a reservoir without creating any significant increase in resistance over an anesthesia bag which has been conventionally used in the past. The counterweighting of the bellows therefore serves as a means for minimizing the resistance and negating the requirements for an anesthesia bag to overcome inspiratory resistance.

The anesthesia unit, by removing excess anesthesia gases from the distal expiratory airway at the end of the expiration and beginning of inspiration, physiological gases with highest carbon dioxide content are vented from the breathing circuit.

Although the anesthesia unit has been disclosed as being used without an anesthesia bag, it should be appreciated that the non-rebreathing valve assembly of the type disclosed U.S. Pat. No. 3,842,828, which includes a compression bulb as therein described, can be connected to the tee 716 of the bellows assembly to permit the bellows assembly to be manually servoed by squeezing of the compression bulb. This occurs because gas from the compression bulb cannot flow into the top cabinet because of the directional gating provided in the master venturi assembly 463 and therefore gas displaced from the compression bulb enters into the canister 246 to provide an inspiratory servoing force.

An anesthesist using the anesthesia unit can visually observe the tidal volume being utilized by the patient by merely examining the travel of the bellows 256 within the transparent canister 246.

The anesthesia unit has an additional advantage in that subambient pressures within the hospital vacuum system cannot cross the gate provided by the valve member 722 in the gas balance valve assembly 718. The valve member 722 is only moved to the open position under the force of arm 726 carried by the master cam member 291.

The automatic refill system as provided in the anesthesia unit prevents a failure from occurring which could be due to an anesthesist failing to observe the progressive depletion of anesthesia gases in the bellows 256.

It is apparent from the foregoing that there has been provided an improved respirator and/or ventilator and a method which is particularly useful in connection with ventilating patients with air and/or oxygen or a mixture of the same with anesthesia gases. The respirator is of a modular construction which makes it relatively inexpensive to manufacture. Many different functions can be obtained. In addition, the respirator can be readily disassembled for repair purposes and assembled. The respirator is provided with a control which forces the patient to exhale against a positive pressure above atmospheric during a predetermined portion of the exhalation phase. Control means is provided for terminating the application of the positive pressure against which the patient must exhale so that the patient is exposed to ambient atmospheric pressure prior to initiation of the inhalation phase. The respirator has been provided with volume limiting capabilities so that precise volumes of gas can be delivered to the patient regardless of such variations caused by temperature changes, changes in compliance and the like. In connection with the volume limiting feature, there is a one for one transfer of gases which are used for aiding the bellows and which are subsequently used for filling the bellows. A relatively simple dial assembly which serves as a gas volume computer is provided for performing this function. The construction of the bellows assembly is such that it can be readily removed for aseptic purposes. Intermittent mandatory ventilation can be provided which also permits the patient to breathe spontaneously before a mandated volume is delivered to the patient. Great flexibility has been provided in adjusting the time of the inhalation and exhalation phases. The respirator has been provided with multiple means for causing the commencement of an inspiratory phase which includes pressure, time and volume.

The respirator is provided with means whereby the patient can readily obtain gases upon demand. The mandated volume is delivered to the patient with a control valve back-up should the patient fail to take a spontaneous breath. When used as an anesthesia unit, gas balancing means is provided to insure that the proper amount of gas is always present in the bellows for delivery to the patient during the next inhalation phase.

I claim:

1. In a respirator having an inhalation phase and an exhalation phase in its operative cycle, an inlet adapted to be connected to a source of gas under pressure, first and second outlets, a sequencing servo having an inlet connected to the inlet of the respirator, said sequencing servo also having an outlet, control valve means disposed in said sequencing servo and movable between open and closed positions to control the flow of gas from the inlet to the outlet of the sequencing servo, said control valve means being in an open or on position during the inhalation phase of the respirator and in a closed or off position during the exhalation phase of the respirator, a patient adapter, means for connecting the outlet of the sequencing servo to the first outlet of the respirator, means for supplying gas from the first outlet of the respirator to the patient adapter, an exhalation valve assembly connected to the patient adapter and movable between open and closed positions and in the open position permitting gases to flow from the patient adapter and in the closed position preventing the flow of gases from the patient adapter, means for supplying gas from the inlet of the respirator to the second outlet of the respirator, means for supplying gas from the second outlet of the respirator to the exhalation valve assembly to maintain the exhalation valve assembly in a closed position during the inhalation phase, means for sensing the pressure of the gas in the first outlet and for switching the sequencing servo from an open position to a closed position when a predetermined pressure is reached in the first outlet, means connected to the exhalation valve means for establishing a positive pressure against which the patient must exhale during the exhalation phase and means for terminating the application of positive pressure to the exhalation valve assembly near the end of the exhalation phase so that the patient is exposed to ambient pressure prior to initiation of the inhalation phase.

2. A ventilator as in claim 1 wherein said means for establishing a positive pressure against which the patient must exhale includes an expiratory flow gradient delay cartridge and means connecting said expiratory flow gradient cartridge to the exhalation valve assembly, said expiratory flow gradient delay cartridge delaying the application of the positive pressure until near the end of the exhalation phase.

3. A respirator as in claim 2 wherein said means for terminating the application of the positive pressure includes a positive end expiratory pressure termination cartridge which is connected to the expiratory flow gradient delay cartridge and to the exhalation valve assembly.

4. A respirator as in claim 1 together with means for establishing the period of time covered by the exhalation phase including an expiratory termination cartridge having valve means movable between open and closed positions, means connecting the expiratory termination cartridge to the inlet and to the sequencing servo whereby when the valve means of the expiratory termination cartridge is moved to an open position source gas is supplied to the sequencing servo, expiratory time control valve assembly connected to the expiratory termination cartridge for controlling the rate of bleed off of gas from the expiratory termination cartridge for controlling movement of the valve means of the expiratory termination cartridge from the closed to an open position, an auxiliary gas reservoir and adjustable orifice means connecting said auxiliary reservoir between said expiratory termination cartridge and said expiratory time control valve assembly.

5. A ventilator as in claim 1 together with means for supplying intermittent mandatory ventilation to the patient.

6. A respirator as in claim 5 wherein said means for supplying intermittent mandatory ventilation includes demand flow accelerator means having an inlet and an outlet and valve means controlling the flow of gases from the inlet to the outlet for supplying gases to the patient upon demand of the patient, means connecting the inlet of the demand flow accelerator means to the inlet of the respirator, means connecting the outlet of the demand flow accelerator to the first outlet of the respirator and means connecting the demand flow accelerator means to the patient breathing circuit for sensing the gases in the patient breathing circuit for moving the valve means of the demand flow accelerator means to permit flow of gases from the inlet to the outlet.

7. A respirator as in claim 6 wherein said means for sensing the pressure of the gases in the patient breathing circuit includes a sensing venturi and means connecting the sensing venturi to the sequencing servo.

8. A respirator as in claim 7 wherein said means for sensing the pressure of the gases in the patient breathing circuit includes means for monitoring the pressure in the breathing circuit independent of the sensing venturi.

9. A respirator as in claim 1 together with volume means for limiting the gases supplied to the patient by volume, said volume limiting means including a bellows assembly having a canister and a bellows disposed within the canister, piping means in communication with the interior of the bellows and in communication with the first outlet of the respirator, piping means in communication with the interior of the canister and in communication with the output from the sequencing servo, transfer valve means connected between the first and second named piping connected to the interior of the bellows and the piping connected to the interior of the canister and including a valve member movable between open and closed positions which in the open position permits flow between the first and second named piping means and in the closed position prevents flow between the first and second named piping means and forces flow from the second named piping means into the interior of the canister, said transfer valve means including means coupled to the output from the sequencing servo for moving the same to a closed position so that during an inhalation phase, inspiratory gases are supplied to the canister to raise the bellows and force gases contained in the bellows into the first outlet of the respirator and for transfering the gases in the canister to the interior of the bellows during the exhalation phase.

10. A respirator as in claim 9 together with means for adjustably limiting the travel of the bellows within the canister to limit the volume within the bellows so that only a predetermined quantity of gases are transferrred into the interior of the bellows.

11. A respirator as in claim 10 wherein said means for adjusting the travel of the bellows to determine the volume within the bellows includes a shaft coupled to the bellows, a cam member carried by the shaft and adjustable stop means adapted to be engaged by said cam member, said adjustable stop means being movable to limit the travel of the cam member and means for moving said stop member.

12. A respirator as in claim 11 wherein said means for moving the stop member includes a plurality of adjustable dial-like members, said dial like members being adjustable with respect to each other.

13. A respirator as in claim 12 wherein said dial-like members are mounted concentrically with respect to each other and means for locking said dial-like members in predetermined positions with respect to each other.

14. A respirator as in claim 11 together with counterweight means secured to the cam member for counterbalancing the bellows and the parts carried thereby.

15. A respirator as in claim 11 together with transfer switch means engagable by said cam member to cause operation of the transfer switch means and means connected to the inspiratory switch means for causing termination of the inhalation phase.

16. A respirator as in claim 1 together with gas accumulator means, selectively operated means for transfering gas from the accumulator means to the first outlet, and means for supplying gas to the accumulator means during the exhalation phase.

17. A respirator as in claim 9 wherein said bellows is removable from said canister together with quick release means for connecting said bellows to said shaft.

18. A respirator as in claim 11 together with gas balance valve means and means carried by said cam member for actuating said gas balance valve means and means connecting said gas balance means to the interior of said canister whereby in the event there is excess gas in the canister, the excess gas may be brought from the canister.

19. A respirator as in claim 11 together with gas refill means engagable by the cam member for introducing additional gas into the bellows when an insufficient quantity of gas is present in the bellows.

20. In a respirator having an inhalation phase and an exhalation phase in its operative cycle, an inlet adapted to be connected to a source of inspiratory gases under pressure, first and second outlets, a sequencing servo having an inlet, means connecting the inlet of the sequencing servo to the inlet of the respirator, said sequencing servo also having an outlet and control valve means movable between open and closed positions to control the flow of gas from the inlet to the outlet of the sequencing servo, said control valve means being in an open or on position during the inhalation phase of the respirator and in a closed or off position during exhalation phase of the respirator, a patient adapter, means for connecting the outlet of the sequencing servo to the first outlet of the respirator to supply inspiratory gases thereto, means for supplying gas from the first outlet of the respirator to the patient adapter, an exhalation valve assembly movable between open and closed positions and in the open position permitting gases to flow from the patient adapter and in the closed position preventing the flow of gases from the patient adapter, means for supplying gas from the inlet of the respirator to the second outlet of the respirator, means for supplying gas fom the second outlet of the respirator to the exhalation valve assembly to maintain the exhalation valve assembly in a closed position during the inhalation phase, volume limiting means for limiting the inspiratory gases supplied to the patient during the inhalation phase, said volume limiting means including a bellows assembly having a canister and a bellows disposed within the canister, first piping means in communcation with the interior of the bellows and in communication with the first outlet of the respirator, second piping means in communication with the interior of the canister and in communication with the outlet from the sequencing servo for supplying inspiratory gases from the inlet of the respirator to the interior of the canister, transfer valve means connected between the first piping means connected to the interior of the bellows and the second piping means connected to the interior of the canister and including a valve member movable between open and closed positions which in the open position permits flow between the first and second named piping means and forces flow from the second named piping means into the interior of the canister, said transfer valve means including means coupled to the output from the sequencing servo for moving the same to a closed position so that during the inhalation phase, inspiratory gases are supplied to the interior of the canister to raise the bellows and to thereby force inspiratory gases contained in the bellows into the first outlet of the respirator and through the patient adapter and for transferring gases in the canister to the interior of the bellows during the exhalation phase said first and second piping means in combination with said transfer valve means forming the sole means for establishing communication between the interior of the bellows and the interior of the canister.

21. A respirator as in claim 20 together with means for adjustably limiting the travel of the bellows within the canister so that only a predetermined quantity of gases are transferred into the interior of the bellows.

22. A respirator as in claim 21 wherein said means for adjusting the bellows to determine the volume of gases which can be transferred into the bellows includes an adjustable member for preventing movement of the bellows beyond a selected position and means for adjusting the position of said adjustable member.

23. A respirator as in claim 20 together with gas balance means and means engagable by operation of the bellows for eliminating excess gas from the bellows assembly.

24. A respirator as in claim 23 together with refill means engagable by movement of the bellows for introducing additional gas into the bellows assembly when an insufficient quantity of gas is present.

25. In a method for ventilating a patient through the use of a patient adapter from a source of gas under pressure, supplying a main flow of gas to the patient adapter during the inspiratory phase, permitting exhalation of gases from the patient adapter during the exhalation phase, establishing a positive pressure against which the patient must exhale during a portion of the exhalation phase and terminating the application of positive pressure in the exhalation phase near the end of the exhalation phase so that the patient is exposed to ambient pressure prior to initiation of the inhalation phase.

26. In a respirator having an inhalation phase and an exhalation phase in its operative cycle, in inlet adapted to be connected to a source of gas under pressure, first and second outlets, a sequencing servo having an inlet connected to the inlet of the respirator, said sequencing servo also having an outlet, control valve means disposed in siad sequencing servo and movable between open and closed positions to control the flow of gas from the inlet to the outlet of the sequencing servo, said control valve means being in an open or on position during the inhalation phase of the respirator and in a closed or off position during the exhalation phase of the respirator, a patient adapter, means for connecting the outlet of the sequencing servo to the first outlet of the respirator, means for supplying gas from the first outlet of the respirator to the patient adapter, an exhalation valve assembly connected to the patient adapter and movable between open and closed positions and in the open position permitting gases to flow from the patient adapter and in the closed position preventing the flow of gases from the patient adapter, means for supplying gas from the inlet of the respirator to the second outlet of the respirator, means for supplying gas from the second outlet of the respirator to the exhalation valve assembly to maintain the exhalation valve assembly in a closed position during the inhalation phase, means for sensing the pressure of the gas in the first outlet and for switching the sequencing servo from an open position to a closed position when a predetermined pressure is reached in the first outlet, IMV demand flow means having an inlet and an outlet and valve means movable between open and closed positions for controlling the flow of gas between the inlet and the outlet of the IMV demand flow means, means connecting the inlet of the IMV demand flow means to the inlet of the respirator, means connecting the outlet of the IMV demand flow means to the first outlet of the respirator, means connecting the valve means of the IMV demand flow means to the patient breathing circuit whereby when the patient takes a breath a pressure drop will be sensed to cause movement of the valve means of the IMV demand flow means into a position to permit gas to flow from the inlet to the outlet of the IMV demand flow means and to the first outlet of the respirator, IMV assist means having an inlet and outlet and valve means movable between open and closed positions for controlling the flow of gas between the inlet and the outlet, means connecting the inlet of the IMV assist means to the inlet of the respirator, means connecting the outlet of the IMV assist means to the first outlet of the respirator, means connecting the valve means of the IMV assist means to the outlet of the IMV demand flow means whereby when gas passes from the inlet to the outlet of the IMV demand flow means, the valve means of the IMV assist means will be moved to a position to permit gas to flow from the inlet to the outlet of the IMV assist means to the first outlet of the respirator.

27. In a respirator as in claim 26 wherein means connecting the inlet of the IMV demand flow means includes on-off valve means for controlling the operation of said IMV demand flow means.

28. A respirator as in claim 27 wherein said means connecting IMV assist means to the inlet includes on-off valve means for controlling the operation of the IMV assist means.

29. In a respirator having an inhalation phase and an exhalation phase in its operative cycle, an inlet adapted to be connected to a source of gas under pressure, first and second outlets, a sequencing servo having an inlet connected to the inlet of the respirator, said sequencing servo also having an outlet, control valve means disposed in said sequencing servo and movable between open and closed positions to control the flow of gas from the inlet to the outlet of the sequencing servo, said control valve means being in an open or on position during the inhalation phase of the respirator and in a closed or off position during the exhalation phase of the respirator, a patient adapter, means for connecting the outlet of the sequencing servo to the first outlet of the respirator, means for supplying gas from the first outlet of the respirator to the patient adapter, an exhalation valve assembly connected to the patient adapter and movable between the open and closed positions and in the open position permitting gas to flow from the patient adapter and in the closed position preventing the flow of gases from the patient adapter, means for supplying gas from the inlet of the respirator to the second outlet of the respirator, means for supplying gas from the second outlet of the respirator to the exhalation valve assembly to maintain the exhalation valve assembly in a closed position during the inhalation phase, means for switching the control valve means of the sequencing sevo from closed to open positions to determine the length of the inhalation and exhalation phases, said switching means including means for establishing the period time covered by the exhalation phase including expiratory termination means having an inlet and an outlet and valve means between open and closed positions, a diaphragm for controlling movement of the valve means and a chamber formed on one side of the diaphragm, means connecting the inlet of the expiratory termination means to the inlet of the respirator, means connecting the outlet of the expiratory termination means whereby the flow of gas through the expiratory termination means between the inlet and the outlet will cause movement of the control valve means of the sequencing servo from a closed to an open position, means for supplying gas under pressure the chamber to cause the diaphragm to move the valve means of the expiratory termination means from an open to a closed position to prevent the flow of gas from the inlet to the outlet of the expiratory termination means, means for bleeding off gas from the chamber of the expiratory termination means at a controlled rate to permit movement of the valve means of the expirtory termination means from a closed to an open position, said last-named means including valve means coupled to said chamber for adjusting the rate of the bleed-off of gas from said chamber, an auxiliary reservoir, one-way check valve means connecting the reservoir to said chamber to permit the flow of gas into the auxiliary reservior and adjustable orifice means connecting the auxiliary reservoir to the valve means for bleeding air from the auxiliary.

30. In a respirator having an inhalation phase and an exhalation phase in its operative cycle, an inlet adapted to be connected to a source of gas under pressure, first and second outlets, a sequencing servo having an inlet adapted to be connected to the source of gas under pressure, first and second outlets, a sequencing servo having an inlet, means connecting the inlet of the sequencing servo to the inlet of the respirator, said sequencing servo also having an outlet and control valve means movable between open and closed positions to control the flow of gas from the inlet to the outlet of the sequencing servo, said control valve means being in an open or on position during the inhalation phase of the respirator and in a closed or off position during the exhalation phase of the respirator, a patient adapter, a patient adapter, means connecting the outlet of the sequencing servo to the first outlet of the respirator to the supply of gases thereto, means for supplying gas from the first outlet of the respirator to the patient adapter, an exhalation valve assembly movable between open and closed positions and in the open position permitting gas to flow from the patient adapter and in the closed position preventing the flow of gas from the patient adapter, means for supplying gas from the inlet of the respirator to the second outlet of the respirator, means for supplying gas from the second outlet of the respirator to the exhalation valve assembly to maintain the exhalation valve assembly in a closed position during the inhalation phase, volume limiting means for limiting the gas supply to the patient during the inhalation phase, said volume limiting means including a valve assembly having a canister and a bellows disposed within the canister, means for supplying gas from the inlet of the respirator to the interior of the canister, means for transferring gases from the interior of the canister to the interior of the bellows and means for adjustably limiting the travel of the bellows within the canister so that only a predetermined quantity of gases are transferred into the bellows, said means for adjustably limiting the travel including a movable stop adapted to limit travel of said bellows, a rotatable shaft, a flexible elongate member movable by rotation of said shaft to move said movable stop member a plurality concentrically mounted dial-like members carried by said shaft for rotating said shaft and being rotatably adjustable with respect to each other and means for locking said dial-like members in predetermined positions with respect to each other.

31. A respirator as in claim 30 together with gas balance valve means connected to the interior of the canister for discharging gas through the gas balance means when there is an excess of gas in the canister.

32. A respirator as in claim 30 together with counterbalance means for counterbalancing the bellows.

* * * * *